United States Patent [19]

Mookherjee et al.

[11] Patent Number: 5,355,718
[45] Date of Patent: Oct. 18, 1994

[54] AROMA EMISSION ANALYSIS SYSTEM

[75] Inventors: Braja D. Mookherjee, Holmdel; Robert W. Trenkle, Brielle; Subha M. Patel, Bridgewater, all of N.J.

[73] Assignee: International Flavors & Fragrances Inc., New York, N.Y.

[21] Appl. No.: 92,463

[22] Filed: Jul. 16, 1993

Related U.S. Application Data

[63] Continuation-in-part of Ser. No. 988,337, Dec. 9, 1992, Pat. No. 5,269,169.

[51] Int. Cl.⁵ .................... G01N 30/86; G01N 33/48
[52] U.S. Cl. .................... 73/23.34; 73/23.42; 47/69
[58] Field of Search .............. 73/23.43, 23.34; 47/69, 47/1.01

[56] References Cited

U.S. PATENT DOCUMENTS

| | | | |
|---|---|---|---|
| 2,226,951 | 12/1940 | Simpson | 47/69 |
| 2,837,912 | 6/1958 | Moncrieff | 73/23.34 |
| 3,557,945 | 1/1971 | Gourio | 47/69 |
| 3,605,335 | 9/1971 | Maitland | 47/69 |
| 3,939,607 | 2/1976 | Spector | 47/69 |
| 4,128,966 | 12/1978 | Spector | 47/69 |
| 4,474,889 | 10/1984 | Terry et al. | 734/23.42 |
| 4,520,651 | 6/1985 | Litman | 73/23.34 |
| 4,597,220 | 7/1986 | Bourrié et al. | 47/69 |
| 5,136,805 | 8/1992 | Mookherjee et al. | 47/69 |
| 5,263,359 | 11/1993 | Mookherjee et al. | 73/23.34 |
| 5,269,169 | 12/1993 | Trenkle et al. | 73/23.34 |

FOREIGN PATENT DOCUMENTS

| | | | |
|---|---|---|---|
| 532556 | 5/1990 | European Pat. Off. | |
| 0222550 | 1/1990 | Japan | 73/23.34 |
| 2115757 | 4/1990 | Japan | 73/23.34 |
| 4181150 | 6/1992 | Japan | 73/23.34 |

OTHER PUBLICATIONS

Mookherjee, et al, J. Ess. Oil. Res. vol. 2, pp. 85–90, (Mar./Apr. 1989), title: "Live vs. Dead Part II. A comparative Analysis of The Headspace Volatiles of Some Important Fragrance and Flavor Raw Materials".

Primary Examiner—Thomas P. Noland
Assistant Examiner—J. David Wiggins
Attorney, Agent, or Firm—Arthur L. Liberman

[57] ABSTRACT

Described is a process for qualitatively and quantitatively substantially continuously analyzing the aroma emitted and rates of emission of the aroma components thereof from two or more different varieties and/or species of living flowers at a given point in time or over a given time period using a single enclosure to contain the living flowers and having aroma trapping means attached to the single enclosure and apparatus for carrying out such process. Also described is a process for preparing one or more perfume compositions comprising the steps of carrying out the aforementioned analysis or analyses and then, using the results of such analysis or analyses, providing and admixing at least the major components found in the analysis or analyses; apparatus for carrying out such process and perfume compositions prepared using such apparatus and process.

47 Claims, 21 Drawing Sheets

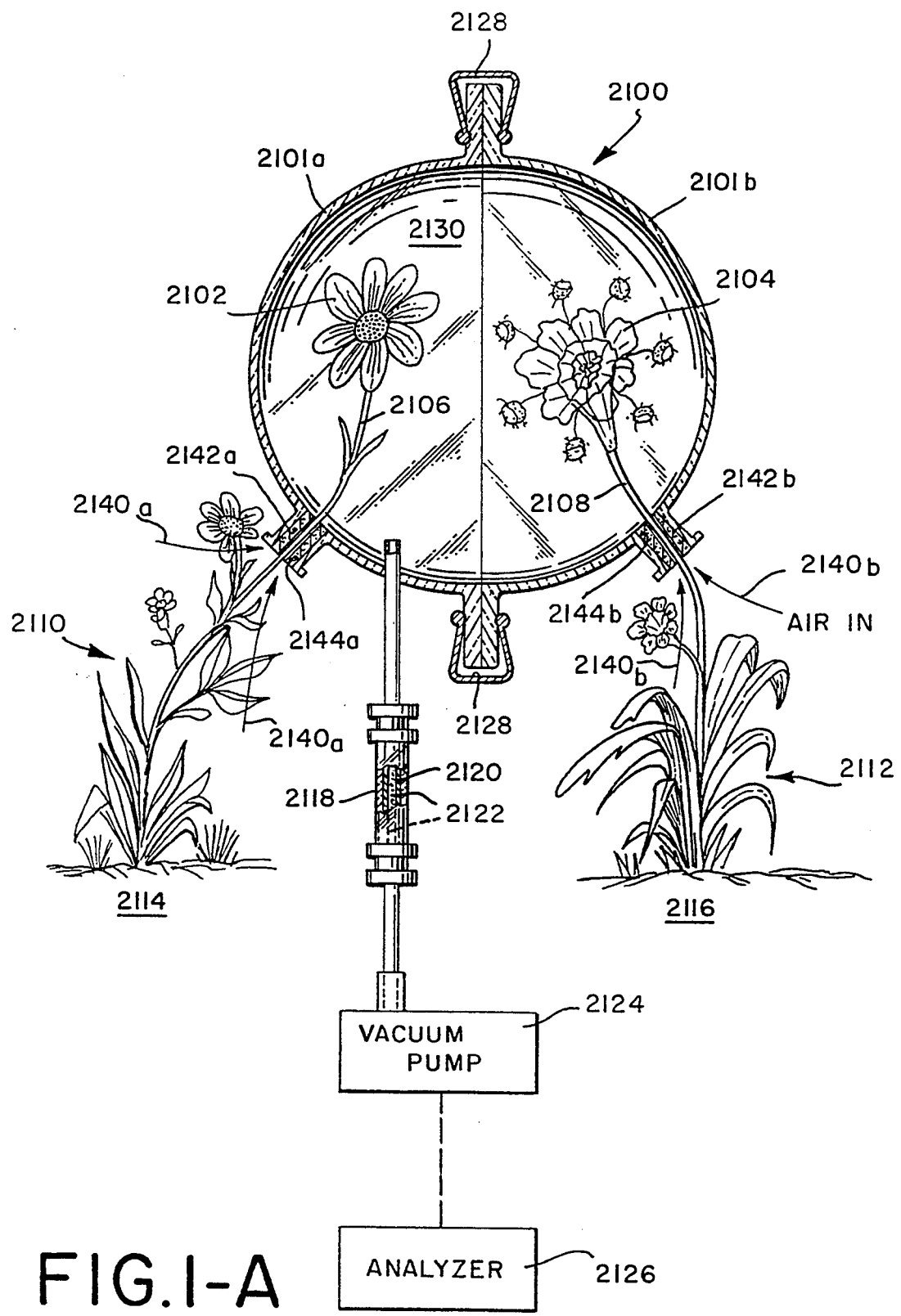
FIG.1-A

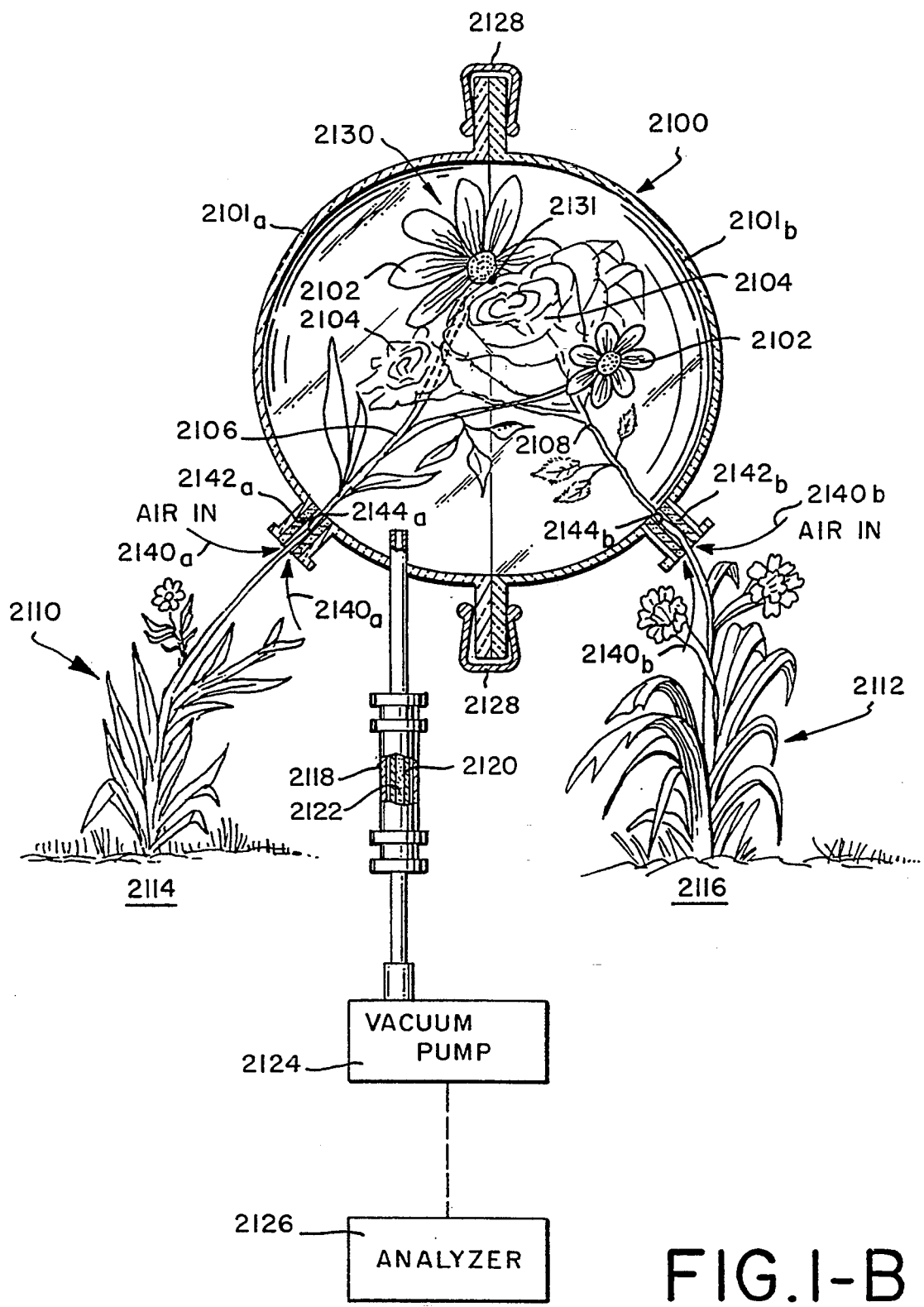
FIG.1-B

GC MASS SPECTRUM

GC MASS SPECTRUM

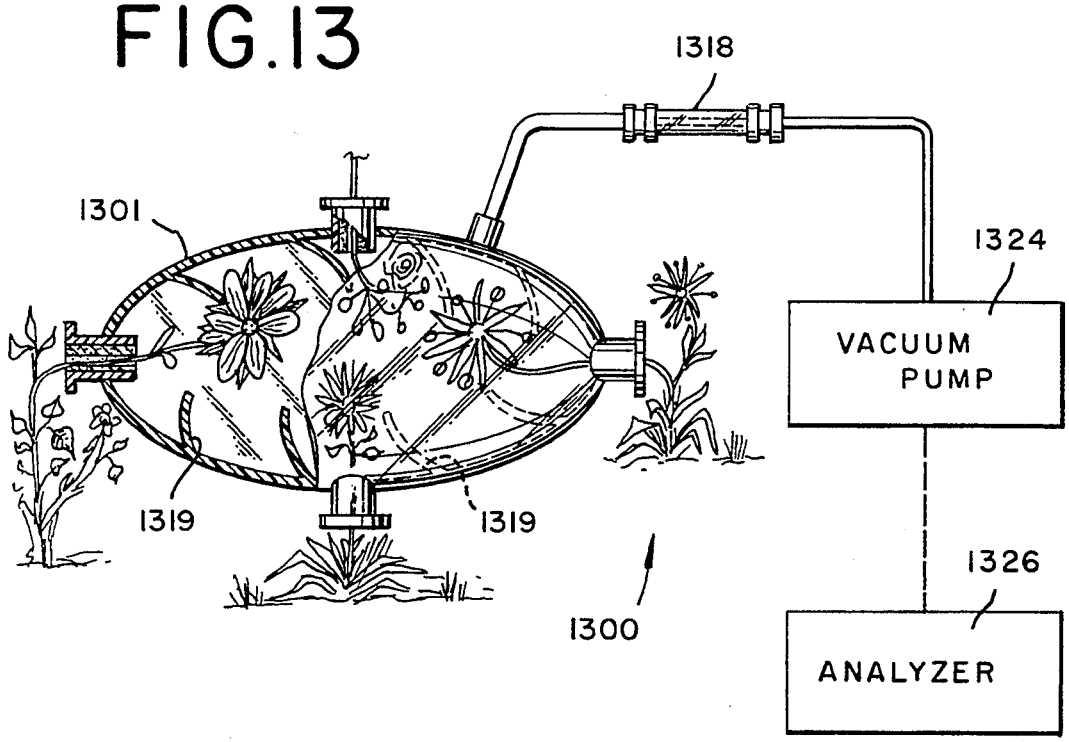
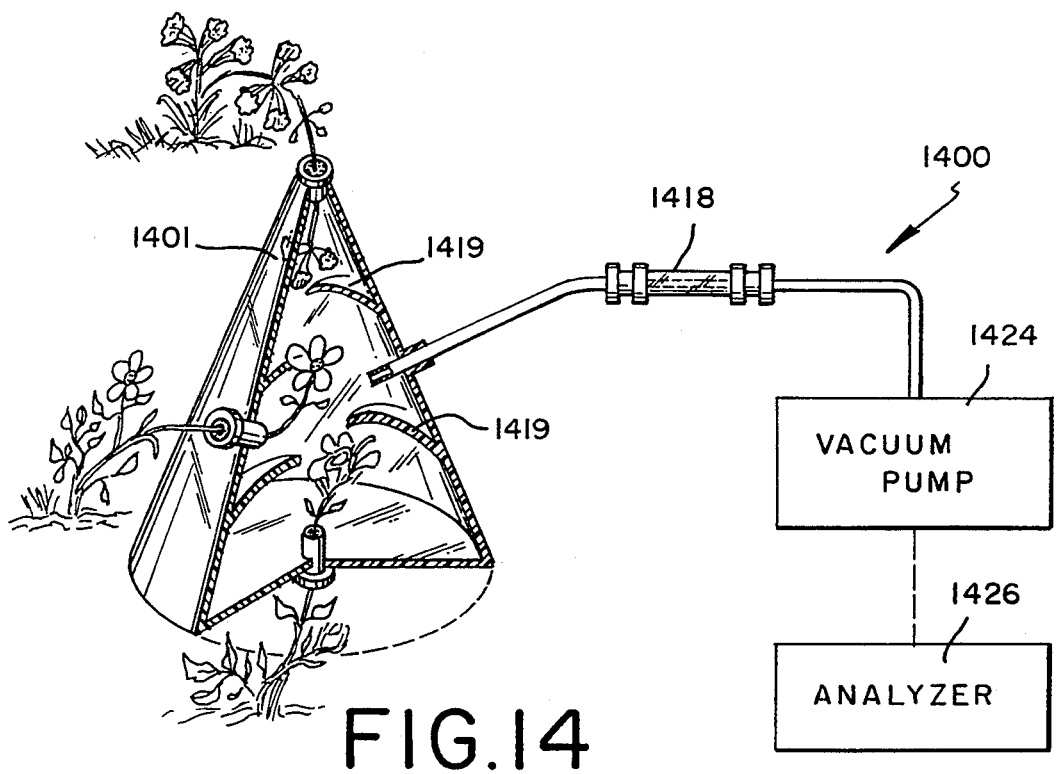

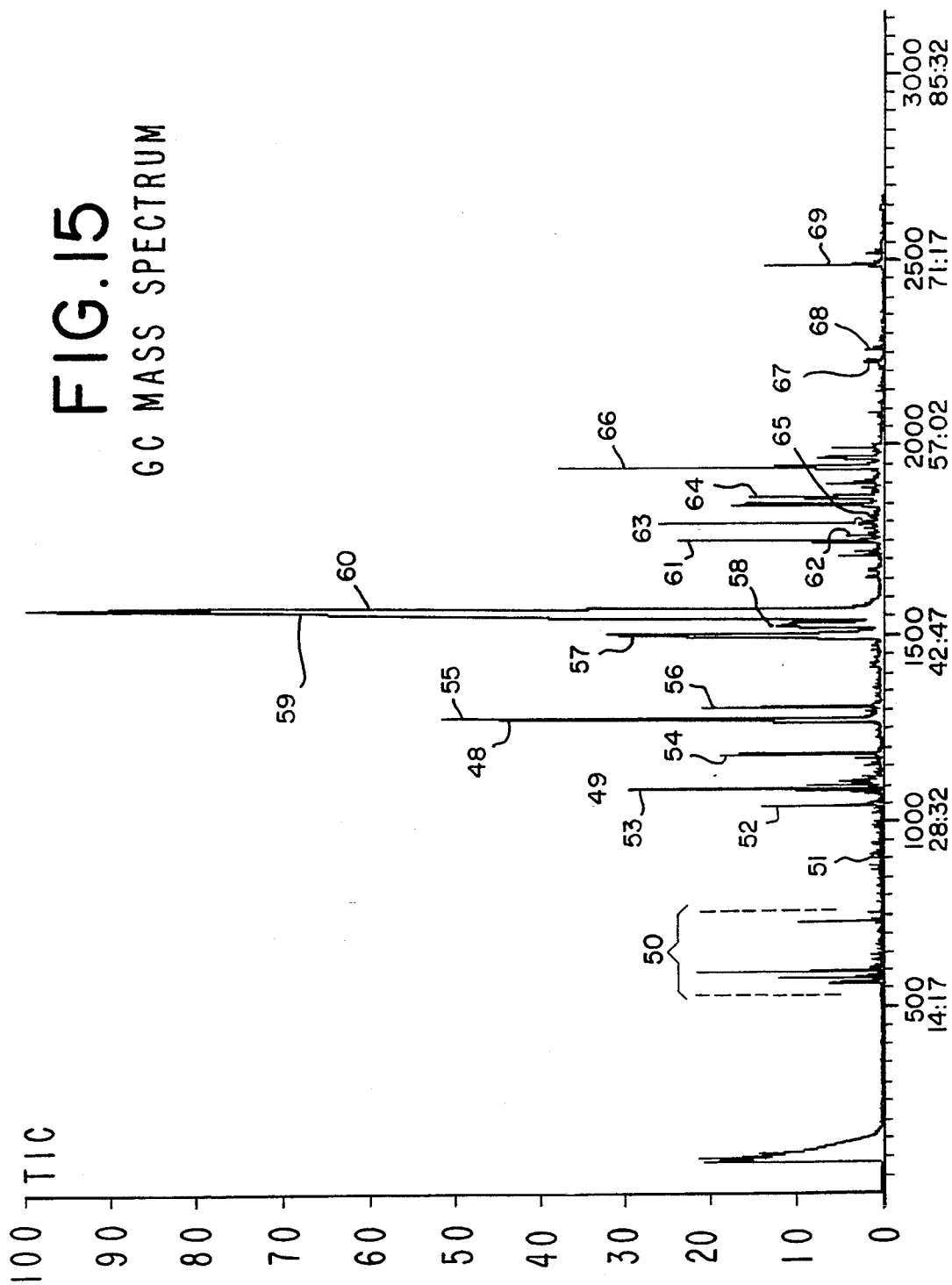

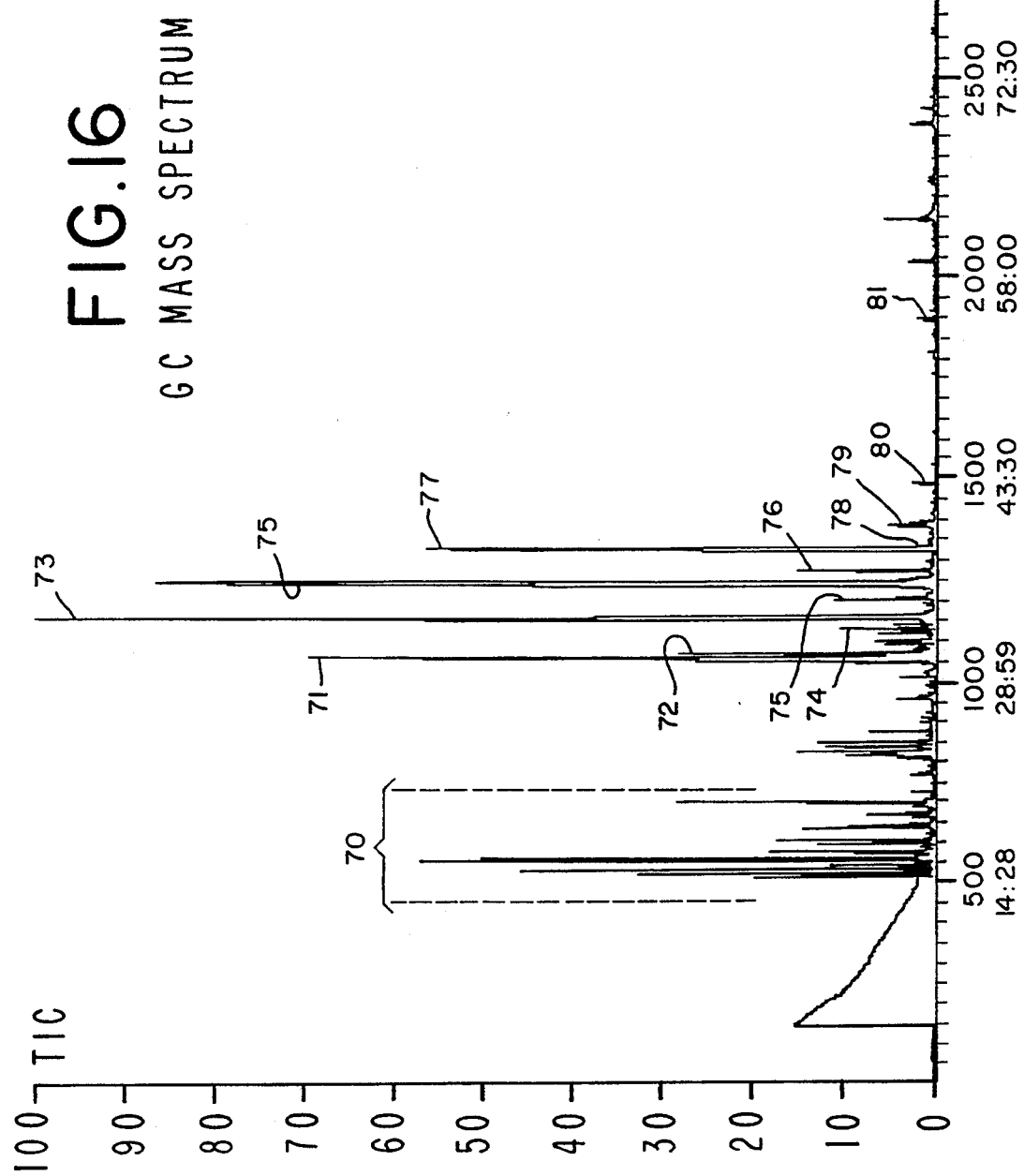

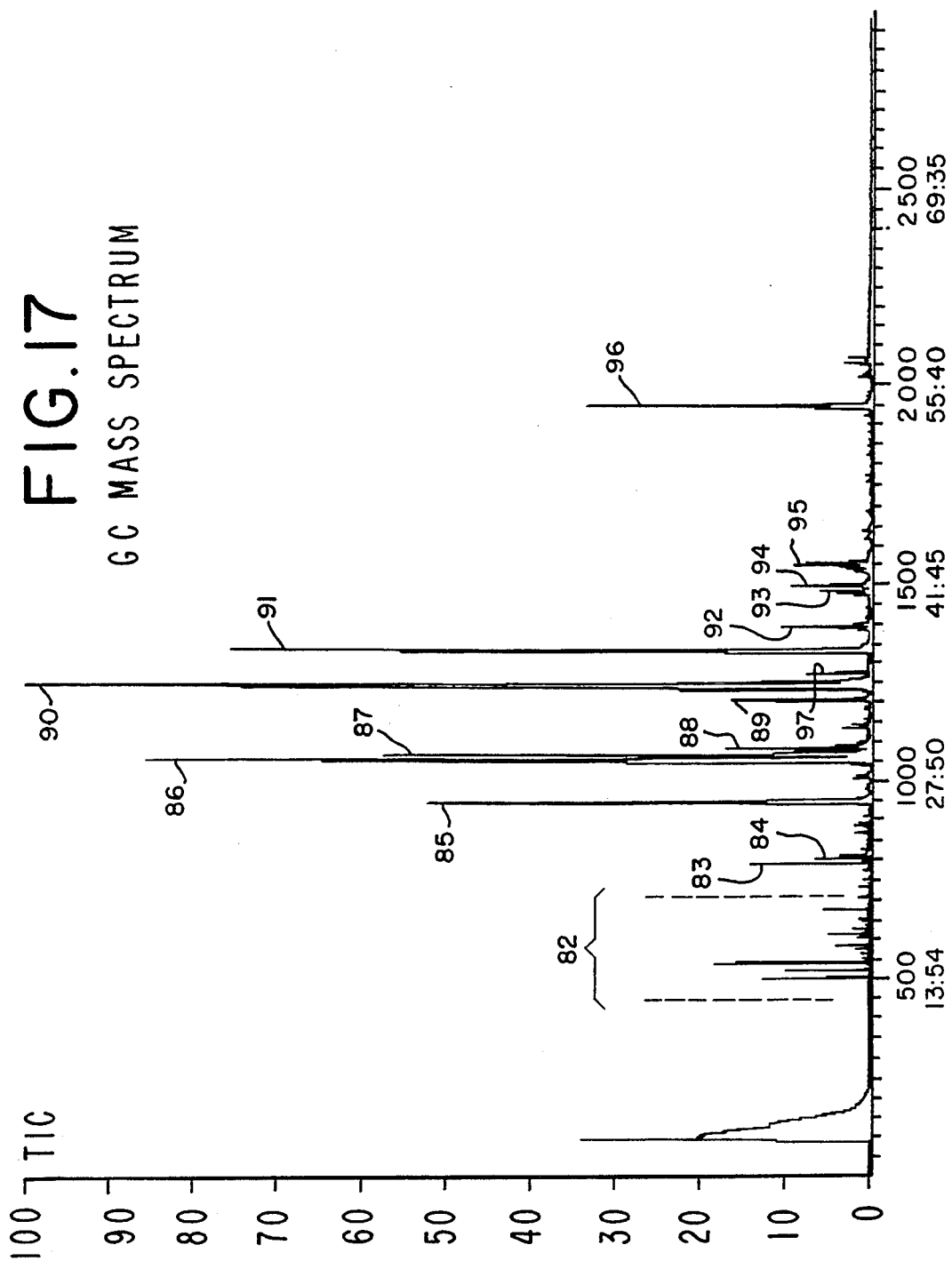

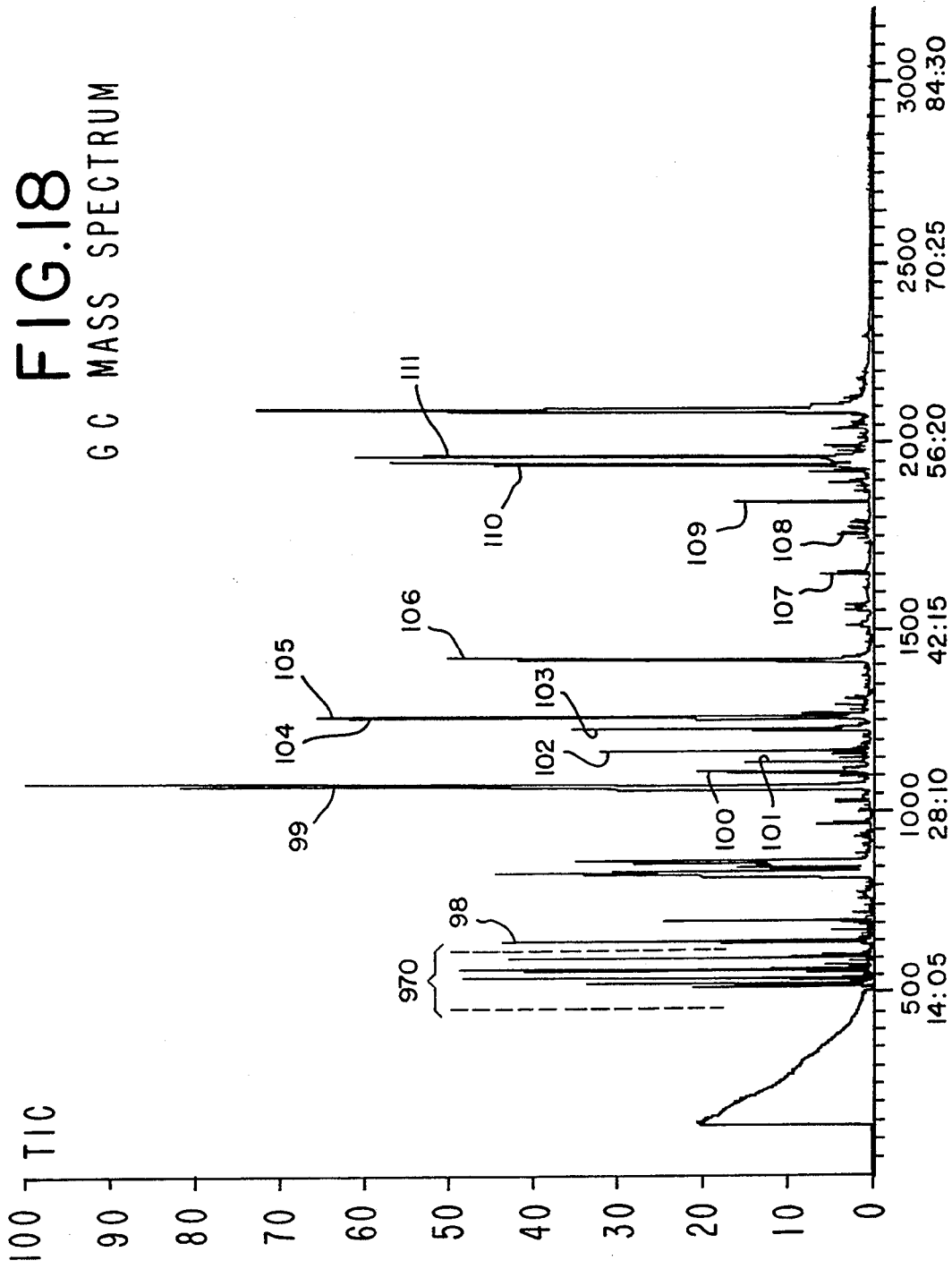

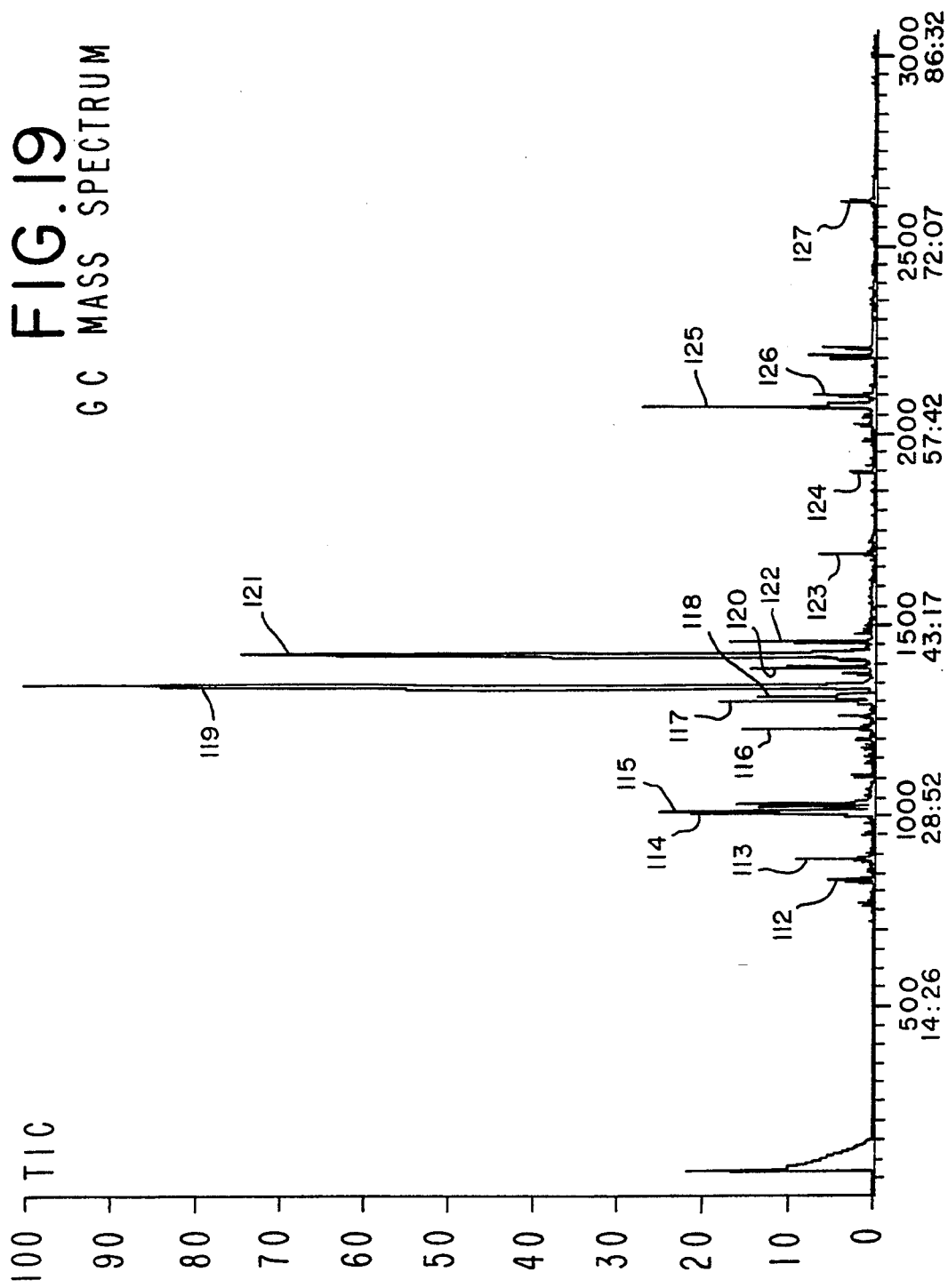

AROMA EMISSION ANALYSIS SYSTEM

COPENDING RELATED PATENT APPLICATIONS

This application is a continuation-in-part of application for U.S. patent Ser. No. 988,337 filed on Dec. 9, 1992 now U.S. Pat. No. 5,269,169 issued on Dec. 14, 1993.

BACKGROUND OF THE INVENTION

Our invention concerns a process for qualitatively and quantitatively substantially continuously analyzing the aroma emitted and rates of emission of the aroma components thereof from two or more different varieties and/or species of living flowers at a given point in time over a given time period using a single enclosure to contain the living flowers and having aroma trapping means attached to the single enclosure and apparatus for carrying out such a process. Our invention also concerns a process for preparing one or more perfume compositions comprising the steps of carrying out the aforementioned analysis or analyses and then, using the results of such analysis or analyses providing and admixing at least the major components found in the analysis, apparatus for carrying out such process, perfume compositions prepared using such apparatus and process, and perfumed articles and colognes containing such perfume compositions.

Uses of aromas evolved from living flowers which are part of living plants or which are parts of living trees are highly sought after in the perfumery and flavor arts. Great difficulty has been experienced in attempting to capture and reproduce actual aroma ingredients of such living flowers at various points in time relative to the maturation of the plant or tree on which the living flower is growing.

In addition, a need has arisen for observation of the growth of living flowers and a need for measuring such growth, standardizing the measurements of such growth at various times of plant or tree maturation and observing such growth has arisen; in an effort to optimize the marketing of perfume compositions based on living flower components.

Mookherjee, et al, J. Ess. Oil Res., Volume 2, pages 85–90, (March/April 1989) title "Live vs. Dead. Part II, A Comparative Analysis of the Headspace Volatiles of Some Important Fragrance and Flavor Raw Materials" sets forth an examination of the headspace volatiles of living and picked tea rose, narcissus, osmanthus and spearmint comparatively using TENAX ® as the trapping adsorbent and GC/MS analysis ("Gas Chromatography/Mass Spectral Analysis") as the method of analysis. Mookherjee, et al discloses that it was found that the living rose possessed cis-3-hexenyl acetate (20.67%) as the major volatile component, whereas the major volatile component of the picked rose was 3,5-dimethoxy toluene. Mookherjee, et al further states that living narcissus flowers were found to contain benzyl acetate (44.0%), 3,4- and 3,5-dimethoxy toluene (35.0%) and indole (5.0%) whereas picked flowers contain benzyl acetate (30.43%), 3,4- and 3,5-dimethoxy toluene (18–39.5%) and indole (0.3–1.0%). Mookherjee, et al further states that osmanthus flowers (living) were found to possess beta-damascenone, dihydro-beta-ionol, and 4-keto-beta-ionone whereas these compounds were not detected in either air or nitrogen-purged picked flowers. Mookherjee further states that harvested spearmint possessed carvone (70.0%) and limonene (2.0%) in its headspace while the headspace of living spearmint was found to contain carvone (24.0%) and limonene (18.0%). Thus, Mookherjee, et al demonstrated that dramatic chemical changes take place in a plant or flower once it is harvested.

What is not disclosed in the prior art is the fact that when two or more different varieties and/or species of living flowers are placed in the same enclosed 3-space, the resulting aroma is different in kind from the separate analyzed aromas of the separate living flowers and such difference gives rise to unexpected, unobvious and advantageous perfume compositions which have unobvious natural aroma qualities (that is, topnotes, middle notes and undertones).

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the headspace in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Pat. No. 5,136,805 does not teach or infer a technique for quantitatively and qualitatively substantially continuously analyzing the aroma emitted and rates of emission of the components thereof of two or more varieties and/or species of living flowers growing from plants or trees in a natural habitat where the plants or trees bearing such flowers are outside of the enclosure containing the living flowers.

THE INVENTION

Our invention covers a process for quantitatively and qualitatively substantially continuously analyzing the aroma emitted and rates of emission of the aroma components thereof from two or more different varieties and/or species of living flowers connected via stems to living trees and/or living plants at a given point in time or over a given period of time, using a single enclosure to contain solely the living flowers attached to small portions of their stems and having aroma trapping means attached to the single enclosure; and apparatus for carrying out such process. Our invention is also intended to cover a process for preparing one or more perfume compositions comprising the steps of carrying out the aforementioned analysis or analyses and then using the results of such analysis or analyses, providing and admixing at least one of the major components found in the analysis or analyses, and apparatus for carrying out such process as well as perfume compositions prepared using such apparatus in process and perfumed articles and colognes containing such perfume compositions.

The process for quantitatively and qualitatively analyzing the emitted aroma and rates of emission of the aroma components thereof from a plurality of n members of two or more different species and/or varieties of living flowers (wherein n is an integer greater than or equal to two) concerns, for example, such groups of species and/or varieties of flowers as follows:

Group A
*Rosa Centifolia*
*Rosa gallica officinalis*
Flowers of the Rose Plant "Ausleap" as disclosed in U.S. Plant Patent 8153 issued on February 23, 1993, the specification for which is incorporated by reference herein.
Flowers from the Rose Plant-"Auscrim" as disclosed in U.S. Plant Patent 8154 issued on February 23, 1993, the specification of which is incorporated herein by reference.
Flowers from the Gazania plant called "Moorpark Yellow" as disclosed in U.S. Plant Patent 8161 issued on February 23, 1993 the specification for which is incorporated herein by reference.
Group B
*Crinum x powellii*
Flowers from the Carnation Plant named CFPC Day Dream as disclosed in U.S. Plant Patent 8232 issued on May 18, 1993 the disclosure of which is incorporated herein by reference.
Flowers from the Chrysanthemum Plant-Alhacultivar disclosed in U.S. Plant Patent 8227 issued on May 11, 1993 the specification for which is incorporated by reference herein.
Group C
*Mahonia japonica*
Flowers from the Rose Plant-"Ausram" as disclosed in U.S. Plant Patent 8156 issued on February 23, 1993 the disclosure for which is incorporated herein by reference.
Flowers from the Rose Plant-"Ausmit" as disclosed in U.S. Plant Patent 8157 issued on February 23, 1993 the specification for which is incorporated herein by reference.
Flowers from the Rose Plant-"Poulbero Variety" as disclosed in U.S. Plant Patent 8230 issued on May 18, 1993 the disclosure for which is incorporated herein by reference.
Group D
*Viola odorata* (sweet violet)
Flowers from the Rose Plant-"Jacosos" as disclosed in U.S. Plant Patent 8235 issued on May 25, 1993 the disclosure for which is incorporated by reference herein.
Flowers from the Chrysanthemum Plant-"Funrise Cultivar" as disclosed in U.S. Plant Patent 8241 issued on May 25, 1993 the disclosure for which is incorporated herein by reference.
Flowers from the Miniature Rose Plant-"Meinochot Variety" as disclosed in U.S. Plant Plant 8242 granted on June 1, 1993 the disclosure for which is incorporated herein by reference.
Flowers from the Chrysanthemum Plant named "Dark Eyes" as disclosed in U.S. Plant Patent 8244 issued on June 1, 1993 the disclosure for which is incorporated herein by reference.
Group E
White Jasminum Nitidum
Peach Colored Rose Fragrant Delight
Group F
Yellow Osmanthus Olive
Peach Rose Fragrant Delight
Group G
Ginger Lily Flower
Jasminum Odoratissimum Flower
Group H
Purple Heliotroprium Iowa
Jasminum Odoratissimum Flower
Group J
Dwarf Navel Orange Flower
Jasmin Nitidum Flower
Group K
Red Rose All That Jazz
White Ginger Lily Flower.

Each of the living flowers is attached through a stem to a living plant or a living tree, the plurality of n members of the living flower group being located within a single totally enclosed 3-space having an outer side and an inner side, the inner side entirely surrounding all of the end living flowers. Examples are the "single totally enclosed 3-space" are:

a sphere
a bifurcated sphere
a right circular cylinder
a right circular cone
an ellipsoid
a frustum of a right circular cone
a tetrahedron.

The process of our invention covers the steps of:

(a) providing a hollow enclosure having
 (i) an outer wall containing at least $n+1$ outer wall orifices spaced at a distance of at least $d_1$ from one another in order to provide for the unobstructed individual maintenance of each of the living flowers, each orifice having an orifice wall surrounding the orifice;
 (ii) having an inner void having a volume $V_0$ sufficient to provide for the separate individual unobstructed maintenance of each of the living flowers; and
 (iii) having an inner volume $V_0$ such that the volume relationship between the volume of the inner void expressed as $V_0$ and the volume of the 3-space surrounding each living flower being $V_i$, the individual flower surrounding 3-space is:

$$V_0 > \sum_{i=2}^{n} V_i;$$

wherein $$V_i = \frac{4}{3} \pi R_i^3;$$

-continued $$V_0 > \sum_{i=2}^{n} \frac{4}{3} \pi R_i^3;$$

and $$V_0 = H + \sum_{i=2}^{n} \frac{4}{3} \pi R_i^3$$

$V_i$ having an individual mathematically constructed outer surface and $$\sum_{i=2}^{n} V_i$$

having an outer surface wherein $R_i$ represents the length of the longest petal of the $i^{th}$ living flower and H is the headspace between the mathematically constructed outer surface of $$\sum_{i=2}^{n} V_i$$

and said inner wall of said single totally enclosed 3-space;

(b) causing the insertion of each of the n members of the plurality of living flowers through a separate outer wall orifice whereby the stem of each living flower is held in place by means of the gripping action of the orifice wall of each of said orifices and whereby each living flower is held in place within said hollow enclosure with the mathematically constructed surface $S_i$ of each living flower being at a finite distance $d_2$ from its assigned orifice; either in contact with or at a finite distance $d_3$ from the mathematically constructed surface $S_i$ of each of its neighboring living flowers and at a finite distance $d_4$ from any inner wall of said hollow enclosure;

(c) trapping the components of the emitted aroma in trapping tube means containing a trapping material with the trapping tube means being engaged with and juxtaposed to at least one of the orifices at a location outside the hollow enclosure, the trapping tube means having two ends:

(i) an orifice end sealably juxtaposed with and engaging said orifice wall; and (ii) an outer end at a location outside the hollow enclosure;

(d) exerting a negative pressure on the single totally enclosed 3-space using a vacuum pumping means, with the vacuum pumping means being juxtaposed with and engaging the outer end of the trapping tube means whereby the aroma components are transmitted from the single totally enclosed 3-space into the trapping tube means and onto the trapping material thereby forming an aroma component-bearing trapping material;

(e) removing the aroma component-bearing trapping material from the trapping tube means;

(f) extracting the aroma components from the aroma component-bearing trapping material thereby forming an extracted aroma component composition; and (g) carrying out qualitative and quantitative analyses on the extracted aroma component composition.

The foregoing steps (e), (f) and (g) may, if desired, be carried out over a period of time, repetitively, at the end of specific time intervals, for example, every hour or every day for a period of one or two or three weeks.

Also covered in our invention is a process for preparing a perfume composition which comprises the steps of carrying out the above process followed by providing from at least one independent source at least the major aroma components found by the analysis of step (g) and then admixing the resulting components to form a perfume composition. When the single totally enclosed 3-space is in the shape of an ellipsoid, the volume relationship:

$$V_0 > \sum_{i=2}^{n} V_i$$

is such that:

$$V_0 = 8 \int_0^{\frac{k}{\sqrt{a}}} \int_0^{\sqrt{\frac{k^2}{b} - \frac{ax^2}{b}}} \int_0^{\sqrt{\frac{k^2}{c} - \frac{ax^2}{c} - \frac{by^2}{c}}} dz\,dy\,dx$$

wherein the equation for the ellipsoid is:

$$ax^2 + by^2 + cz^2 = K^2$$

wherein a, b, c and k are the same or different numerical constants and wherein x is a dimensional variable measuring horizontal distance from the geometric center of the ellipsoid to the inner side of the hollow enclosure; wherein y is a dimensional variable measuring vertical distance from the geometric center of the ellipsoid to the inner side of the hollow enclosure; and wherein z is a dimensional variable measuring depth distance from the geometric center of the ellipsoid to the inner side of the hollow enclosure. The relationship from a mathematical standpoint of the diameter, $D_0$ and volume $V_0$ of the single totally enclosed 3-space to the diameter $D_i$ and volume $V_i$ of the individual mathematically constructed outer surface of the $i^{th}$ living flower is shown in the following equations:

$$D_{0max}^3 = 15 \sum_{i=2}^{n} D_i^3$$

$$D_{0max} = 15 \sum_{i=2}^{n} D_i^3$$

$$V_{0min} = 1.5 \sum_{i=2}^{n} V_i$$

$$V_{0max} = 15 \sum_{i=2}^{n} V_i$$

and $$1.5 \sum_{i=2}^{n} V_i \leq V_0 \leq 15 \sum_{i=2}^{n} V_i$$

When the single totally enclosed 3-space wall is fabricated of a semi-rigid transparent substance such as a polyacrylate or polymethacrylate such as polyethylmathacrylate or polymethylmathacrylate or copolymers of methylmathacrylate, ethylmathacrylate and ethylene, then the volume $V_0$ will be subject to change according to the equation:

$$V_0 = V_{01} + \Delta V_0$$

wherein the symbol $$V_{01}$$

is the initial volume and the symbol $$\Delta V_0$$

is the change in volume. This change in volume is shown by the equation $$\Delta V_0 = \int_{\theta_1}^{\theta_2} \frac{\left[\left(\frac{\partial v}{\partial \theta}\right) + \left(\frac{\partial \Sigma V}{\partial \theta}\right) + \left(\frac{\partial T}{\partial \theta}\right) + \left(\frac{\partial P}{\partial \theta}\right)\right] d\theta}{+ \int_{\theta_1}^{\theta_2} \left[\frac{\partial^2 m}{\partial \theta^2}\right] d\theta}$$

where it is assumed that the original volume $V_0$ is:

$$V_0 = f\left(v, \sum_{i=2}^{n} V_i, T, P, \frac{\partial m}{\partial \theta}\right)$$

wherein the symbol $$\sum_{i=2}^{n} V_i$$

is such that $$V_i = \frac{4}{3} \pi R_i^3$$

wherein $R_i$ is the length of the longest petal of the living $i^{th}$ flower and the term represents the total mathematically constructed spherical volumes surrounding the group of living flowers in the totally enclosed 3-space; P represents pressure; T represents temperature; v represents the air velocity within the single totally enclosed 3-space and the symbol:

$$\frac{\partial m}{\partial \theta}$$

represents the partial derivative of the mass transfer of aroma components per unit time from the living flower to the trapping substance. The symbol:

$$\theta$$

represents time. The symbol:

$$\theta_1$$

represents initial time and the symbol:

$$\theta_2$$

represents the time at the end of the measurement. The symbol:

$$\frac{\partial v}{\partial \theta}$$

is actually:

$$\left(\frac{\partial v}{\partial \theta}\right)_{P,T,\frac{\partial m}{\partial \theta}, \Sigma V}$$

and is the partial derivative of air velocity with respect to time. The symbol:

$$\frac{\partial \Sigma V}{\partial \theta}$$

is actually:

$$\left(\frac{\partial \sum_{i=2}^{n} V_i}{\partial \theta}\right)_{P,T,v,\frac{\partial m}{\partial \theta}}$$

and is the partial derivative of the mathematically constructed individual flower volume sum with respect to time. The symbol:

$$\frac{\partial T}{\partial \theta}$$

is actually:

$$\left(\frac{\partial T}{\partial \theta}\right)_{P,v,\Sigma,V_i \frac{\partial m}{\partial \theta}}$$

and is the partial derivative of temperature with respect to time. The symbol:

$$\frac{\partial P}{\partial \theta}$$

is actually:

$$\left(\frac{\partial P}{\partial \theta}\right)_{v,T,\Sigma,V_i \frac{\partial m}{\partial \theta}}$$

and is the partial derivative of internal pressure within the enclosed 3-space with respect to time. The symbol:

$$\frac{\partial m}{\partial \theta}$$

is actually:

$$\left(\frac{\partial m}{\partial \theta}\right)_{P,T,v,\Sigma V_i}$$

The symbol:

$$\frac{\partial^2 m}{\partial \theta^2}$$

is actually:

$$\left[\frac{\partial^2 m}{\partial \theta^2}\right]_{P,T,v,\Sigma V_i} \quad (5)$$

and is the partial derivative of the rate of mass transfer of aroma components from the living flower to the entrapment material with respect to time.

Referring back now to the relationship of $V_0$ to $V_i$, when the 0 is an imperical preferable function of $V_i$ as follows:

$$D_0 = [1.09 + .01\,n] \sum_{i=2}^{n} D_i \quad (15)$$

where n represents the number of living flowers within the enclosed 3-space. The symbol:

$$\sum_{i=2}^{n} D_i$$

represents the arithmetic sum of the mathematically constructed diameters of each living flower enclosed within the single totally enclosed 3-space.

The process of our invention may be further modified wherein radiation from one or more radiation sources such as an infrared radiation source and/or an ultraviolet radiation source connected to an electric power supply is emitted in a direction from one or more radiation sources and is directed into the totally enclosed 3-space containing the living flowers. The radiation source(s) can be a plurality of sources directed to individual living flowers or a single radiation source or a multitude of radiation sources greater than the number of living flowers. The use of such infrared or ultraviolet radiation will give rise to an alteration in the aroma composition and hence the aroma components trapped, evolved by the two or more living flowers contained within the single enclosed 3-space.

Furthermore, a plurality of separate perfume compositions containing at least the major components of the aromas emitted by a multitude of groups of living flowers may be produced by carrying out a process comprising the steps of:

(i) carrying out the aforementioned process;
(ii) separately providing from independent sources at least the major aroma components found by the analyses of each of the steps (g) of the above process; and
(iii) separately admixing each of the groups of components to form separate perfume compositions.

By the same token, the apparatus of our invention for qualitatively and quantitatively substantially continuously analyzing the emitted aroma and rates of emission of the aroma components thereof from a plurality of n members of two or more different species and/or varieties of living flowers wherein n is an integer greater than or equal to two comprises:

(a) two or more adjacently located species and/or varieties of living flowers each of which is attached through a stem to a living plant imbedded in a nutrient medium or to a living tree imbedded in a nutrient medium;
(b) a hollow enclosure having:

(i) an outer wall containing at least n+1 outer wall orifices spaced at a distance of at least $d_1$ from one another in order to provide for the unobstructed individual maintenance of each of said living flowers each orifice having an orifice wall surrounding said orifice;
(ii) having an inner void having a volume $V_0$ sufficient to provide for the separate individual unobstructed maintenance of each of the living flowers; and
(iii) having an inner volume $V_0$ such that the volume relationship between the volume of the inner void expressed as $V_0$ and the volume of the 3-space surrounding each living flower being $V_i$, the individual flower surrounding the 3-space (mathematically constructed) is:

$$V_0 > \sum_{i=2}^{n} V_i$$

wherein $$V_i = \frac{4}{3}\pi R_i^3;$$

$$V_0 > \sum_{i=2}^{n} \frac{4}{3}\pi R_i^3;$$

and $$V_0 = H + \sum_{i=2}^{n} \frac{4}{3}\pi R_i^3$$

$V_i$ having an individual mathematically constructed outer surface and $$\sum_{i=2}^{n} V_i$$

the sum of the mathematically constructed volumes around each of the living flowers having a mathematically constructed outer surface $S_i$ wherein $R_i$ represents the length of the longest petal of the $i^{th}$ living flower and H is the headspace between the mathematically constructed outer surface of $$\sum_{i=2}^{n} V_i$$

and said inner wall of said single totally enclosed 3-space, each of the n members of the plurality of living flowers being inserted through a separate outer wall orifice whereby the stem of each living flower is held in place by means of the gripping action of the orifice walls of each of said orifices and whereby each living flower is held in place within said hollow enclosure with the mathematically constructed surface $S_i$ of $V_i$ of each living flower being at a finite distance $d_2$ from its assigned orifice; and being in contact with or at a finite distance $d_3$ from each of the mathematically constructed surfaces $S_i$ of each of its neighboring flowers and at a finite distance $d_4$ from any inner wall of said hollow enclosure;

(c) engaged with and juxtaposed to at least one of said orifices at a location outside said hollow enclosure trapping tube means containing a trapping material for trapping the components of said emitted aroma, said trapping tube means having two ends:
  (i) an orifice end sealably juxtaposed with and engaging said orifice wall; and
  (ii) an outer end at a location outside the hollow enclosure;
(d) juxtaposed with and engaging said outer end of said trapping tube means, a vacuum pumping means exerting a negative pressure on said single totally enclosed 3-space whereby said aroma components are transmitted from said single totally enclosed 3-space into said trapping tube means and onto said trapping material thereby forming an aroma component-bearing trapping material;
(e) means for removing the aroma component-bearing trapping material from said trapping tube means;
(f) extraction means for extracting the aroma components from the aroma component-bearing trapping material thereby forming an extracted aroma component composition; and
(g) analysis means for carrying out qualitative and quantitative analysis on the extracted aroma component composition.

The apparatus may also be constructed so that one or more radiation sources requiring an electric power supply is located external to and in close proximity to the totally enclosed 3-space wherein radiation from the radiation source is directed into the totally enclosed 3-space thereby altering the rate of evolution of aroma components and the composition of the aroma being evolved by the said two or more living flowers. Furthermore, the totally enclosed 3-space may have baffles bonded to the inside wall of the totally enclosed 3-space causing turbulent mixing of the aroma components of the individual living flowers as said aroma components are evolved from the living flower into the air stream prior to reaching the trapping material.

The analysis means may be GC-MS apparatus (gas chromatography/mass spectral analysis apparatus taken alone or taken further together with infrared analysis equipment and nuclear magnatic resonance analysis equipment. In addition, Raman Spectral analysis equipment may also be used in the analysis means for analyzing the aroma components evolved by the living flowers within the totally enclosed 3-space.

Various trapping materials are useful in the practice of our invention in the trap used in trapping the aroma components emitted from within the totally enclosed 3-space by the living flowers. TENAX ® is a preferable material. Various forms of TENAX ® are useful, for example, TENAX ®-GC. TENAX ® is a registered trademark of ENKA N.V. of The Kingdom of The Netherlands (CAS Registration No. 24938-68-9). Various forms of TENAX ® and methods of producing same are described in the following U.S. Patent, the disclosures of which are incorporated herein by reference:

U.S. Pat. No. 3,400,100 issued on Sep. 3, 1968 ("Process For The Preparation Of Polyphenylene Ethers")
U.S. Pat. No. 3,644,227 issued on Feb. 22, 1972 ("Separation Of Poly(2,6-Dimethyl-1,4-Phenyleneoxide) from its blends with other polymers")
U.S. Pat. No. 3,703,564 issued on Nov. 21, 1972 ("Bis[-Polyphenyleneoxide]-Ester Block Copolymers")
U.S. Pat. No. 4,431,779 issued on Feb. 14, 1984 ("Polyetheramide-Polyphenylene Ether Blends")
U.S. Pat. No. 4,801,645 issued on Jan. 31, 1989 ("Thermoplastic Resin Composition").

TENAX ®-GC is actually a polyphenyleneoxide defined according to the structure:

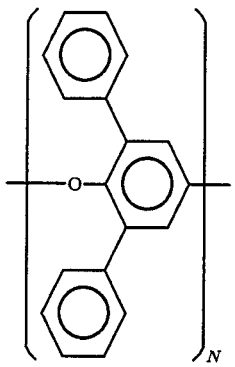

wherein N is an integer of from about 100 up to about 150.

Other trapping materials useful in the practice of our invention are as follows: Activated Carbon marketed by Aldrich Chemical Company of 1001 West Saint Paul Avenue, Milwaukee, Wis. 53233 (Catalog Nos. 16, 155-1; 29, 259-1; 24, 223-3; 24, 224-1 and 24, 227-6); Activated Alumina marketed by Sigma Chemical Company of St. Louis, Mo. (Catalog Nos. A8753; A8878; A9003; A1772; A1522 and A2272); Silica Gels marketed by Sigma Chemical Company, for example, Catalog Nos. S4004; S6628 and H8506; CHROMOSORB ® (registered trademark of the Johns-Manville Company of Manville, N.J.) such as CHROMOSORB ® LC-1; CHROMOSORB ® LC-2; CHROMOSORB ® LC-3, and CHROMOSORB ® LC-7 marketed by the Sigma Chemical Company under Catalog Nos. C 0641, C 0766, C 5517 and C 6269.

The negative pressure pump means of our invention useful in the practice of our invention is preferably a vacuum pump of the "Low Flow" variety, for example, "Low Flow" pumps marketed by the Ametek Company of Largo, Fla. 34643 (the Ametek Constant Flow Sampler).

At least one of the living flower fragrance compositions produced according to the process of our invention and one or more auxiliary perfume ingredients including, for example, alcohols, aldehydes, nitriles, esters, cyclicesters, ketones, ethers, synthetic essential oils and natural essential oils may be admixed so that the combined odors of the individual components produce a pleasant and desired fragrance particularly and preferably in the floral fragrance area.

Such perfume compositions usually contain (a) the main note or "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, it is the individual components which contribute to its particular olfactory characteristics, but the overall effect of the perfume composition will be the sum of the effects of each of the ingredients. Thus, one or more of the living flower fragrance compositions of our invention and one or more auxiliary perfume ingredients can be used to alter the aroma characteristics of a perfume composition, for example, by utilizing or moderating the olfactory reaction contributed by at least one other ingredient in the composition.

The amount of at least one of the living flower fragrance compositions of our invention useful in perfume compositions for augmenting or enhancing of floral, magnolia, and jasmine aromas may vary from about 1% by weight of the perfume composition up to 100% by weight of the perfume composition (the entire composition can be composed of the living flower fragrance components determined by the practice of our invention).

At least one of the living flower compositions of our invention and, if desired, one or more auxiliary perfume ingredients can be used to impart floral aroma nuances, topnotes and undertones to soaps, anionic, cationic, nonionic or zwitterionic detergents, fabric softener compositions, fabric softener articles, cosmetic powders, hair preparations and the like. The amount employed can range up to 100% by weight of the fragrance components and can range up to approximately 0.5% of the weight of the perfumed article and will depend upon considerations of cost, nature of the end product, the effect desired on the finished product and the particular fragrance sought.

At least one of the living flower fragrance compositions of our invention and, if desired, one or more auxiliary perfume ingredients are useful, taken alone or in perfume compositions as olfactory components in anionic, cationic, nonionic or zwitterionic detergents, soaps, fabric softener compositions, fabric softener articles for use in clothes dryers (e.g., "BOUNCE®", a registered trademark of the Procter & Gamble Company of Cincinnati, Ohio), space odorants and deodorants, perfumes, colognes, toilet waters, bath preparations, such as lacquers, brilliantines, creams, deodorants, hand lotions and sun screens; powders such as talcs, dusting powders, face powders and the like.

When used as an olfactory component in perfume compositions or perfumed articles, such as anionic, cationic, nonionic, or zwitterionic detergents and fabric softener compositions and fabric softener articles (e.g., for use in clothing dryers) as little as 0.05% of at least one of the living flower fragrance compositions of our invention and, if desired, one or more auxiliary perfume ingredients will suffice to impart various floral aroma nuances. Generally, no more than 0.05% of at least one of the living flower perfume compositions of our invention and, if desired, one or more auxiliary perfume ingredients based on the ultimate end product is required in the perfumed article.

In addition, the perfume composition or fragrance composition of our invention can contain a vehicle or carrier for at least one of the living flower perfume compositions of our invention and, if desired, one or more auxiliary perfume ingredients. The vehicle can be a liquid such as a non-toxic alcohol, a non-toxic glycol or the like. The carrier can also be an absorbent solid, such as a gum (e.g., gum arabic, xantham gum or guar gum) or components for encapsulating the composition (such as gelatin as by means of coacervation).

It will thus be apparent that at least one of the living flower compositions of our invention and, if desired, one or more auxiliary perfume ingredients can be used to alter the sensory properties, particularly organoleptic properties of a wide variety of consumable materials.

BRIEF DESCRIPTION OF THE DRAWINGS

FIG. 1A is a cut-way side elevation view of one embodiment of the apparatus of our invention wherein a single totally enclosed 3-space is spherical in shape and has contained therein two different species of living flowers the mathematically constructed surfaces of which are at finite distances from one another.

FIG. 1B is another embodiment of the apparatus of our invention showing a cut-away side elevation view of said apparatus wherein the totally enclosed 3-space is spherical in shape and contains within the totally enclosed 3-space two different species of living flowers which are in contact with one another.

FIG. 13 is a partially cut-away side elevation view of another embodiment of the apparatus of our invention wherein the single totally enclosed 3-space is an ellipsoid and contained within the ellipsoid are four different species of living flowers; and affixed to the inner wall of the ellipsoid are baffles.

FIG. 14 is a cut-away schematic perspective diagram of another embodiment of the apparatus of our invention wherein the single totally enclosed 3-space is in the shape of a right circular cone and contained in the right circular cone are two different species of living flowers; and affixed to the inner walls of the right circular cone are baffles.

FIG. 15 is a GC-mass spectrum of the constitution of a composition evolved from two living flowers; Yellow Osmanthus Olive and Peach Rose Fragrant Delight using the apparatus of FIG. 1B according to the procedure of Example II.

FIG. 16 is a GC-mass spectrum for the components of the aroma composition evolved from two living flowers; Ginger Lily Flower and *Jasminum odoratissimum* Flower using the apparatus of FIG. 1B in accordance with the procedure of Example III.

FIG. 17 is the GC-mass spectrum of the composition evolved from two living flowers; Purple *Heliotropium iowa* and *Jasminum odoratissimum* Flower using the apparatus of FIG. 1B in accordance with the procedure of Example IV.

FIG. 18 is the GC-mass spectrum for the aroma components of the aroma composition evolved from two flowers contained in the same single totally enclosed 3-space; Dwarf Navel Orange Flower and *Jasmin nitidum* Flower using the apparatus of FIG. 1B in accordance with the procedure of Example V.

FIG. 19 is the GC-mass spectrum for the aroma components of the composition evolved from the two living flowers; Red Rose All That Jazz and White Ginger Lily Flower contained in the totally enclosed 3-space of FIG. 1B in accordance with the procedure of Example VI.

DETAILED DESCRIPTION OF THE DRAWINGS

Figure 2:
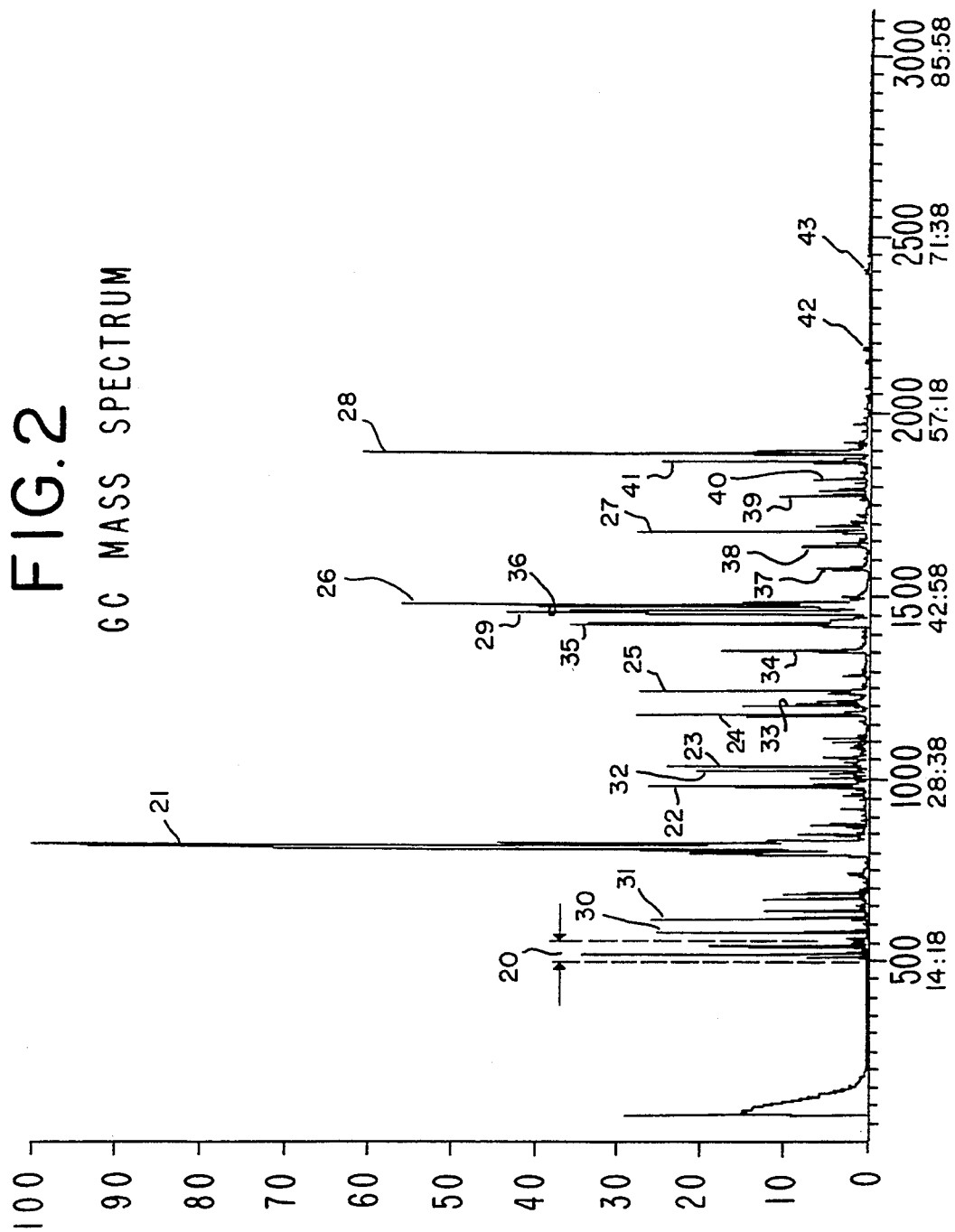
FIG. 2 is a GC-mass spectrum of the aroma components of a composition evolved when white *Jasminum nitidum* and peach colored rose fragrant delight living flowers are contained in a spherical totally enclosed 3-space as set forth in FIG. 1B according to Example I, infra.

FIGS. 1A and 1B set forth apparatus 2100 for qualitatively and quantitatively analyzing the emitted aroma and rates of emission of the aroma components thereof from two flowers, flowers 2104 and 2102 each of which flower is attached through a stem 2108 (for flower 2104) and 2106 (for flower 2102) to a living plant (2112 for flower 2104 and 2110 for flower 2102), the two flowers being located within a single totally enclosed 3-space 2130 having an outer side and an inner side, the inner side entirely surrounding the two living flowers 2104 and 2102. In the apparatus of FIG. 1, the 3-space is enclosed by a sphere composed of two hemispherical sides 2101a and 2101b clamped together using clamps 2128. Flower 2102 contained in the 3-space 2130 is held in place at opening 2144a having a neck 2142a. It should be noted that plant 2112 is growing in the ground 2116. On engaging the vacuum pump 2124, air 2140b and 2140a is past through space 2130 past flowers 2102 and 2104 and then into tube 2120 containing TENAX ®-GC packing 2122, the outer tube being indicated by reference numeral 2118.

Thus, since there are two flowers, the outer wall 2101a and 2101b contains three orifices, two for the flowers and one for the analytical tube. Analyzer 2126 represents GC-mass spectral analytical apparatus. Analyzer 2126 is also intended to include infrared analytical equipment and ultraviolet analytical equipment in addition to the GC-mass spectral analytical equipment. Furthermore, Raman analytical equipment can also be included in "analyzer" 2126. FIG. 1A shows flowers 2102 and 2104 apart whereas FIG. 1B shows flowers 2102 and 2104 in contact with one another at region 2131.

FIG. 2 is the GC-mass spectrum for the headspace resulting from carrying out the procedure of Example I using as the two flowers, White *Jasminum nitidum* and Peach Colored Rose Fragrant Delight. The peaks indicated by reference numeral 20 represent "background" peaks. The peak indicated by reference numeral 30 is for isovaleraldehyde. The peak indicated by reference numeral 31 is for 3-methyl butylronitrile. The peak indicated by reference numeral 21 is for isoamyl acetate. The peak indicated by reference numeral 22 is for 6-methyl-2-hepten-5-one. The peak indicated by reference numeral 32 is for cis-3-hexenyl acetate. The peak indicated by reference numeral 23 is for hexyl acetate. The peak indicated by reference numeral 24 is for methyl benzoate. The peak indicated by reference numeral 33 is for beta-phenylethyl alcohol. The peak indicated by reference numeral 25 is for 4,8-dimethyl-2,3,7-nonatriene. The peak indicated by reference numeral 34 is for methylsalicylate. The peak indicated by reference numeral 35 is for a 1:1 mixture of citronellol and nerol. The peak indicated by reference numeral 29 is for beta-phenylethyl acetate. The peak indicated by reference numeral 36 is for geraniol. The peak indicated by reference numeral 26 is for 3,5-dimethoxy toluene. The peak indicated by reference numeral 37 is for methyl anisate. The peak indicated by reference numeral 38 is for citronellyl acetate. The peak indicated by reference numeral 27 is for geranyl acetate. The peak indicated by reference numeral 39 is for beta-cubebene. The peak indicated by reference numeral 40 is for gamma-cadinene. The peak indicated by reference numeral 41 is for germacrene-D. The peak indicated by reference numeral 28 is for alpha-farnesene. The peak indicated by reference numeral 42 is for heptadecane. The peak indicated by reference numeral 43 is for nonadecane.

Figure 3:
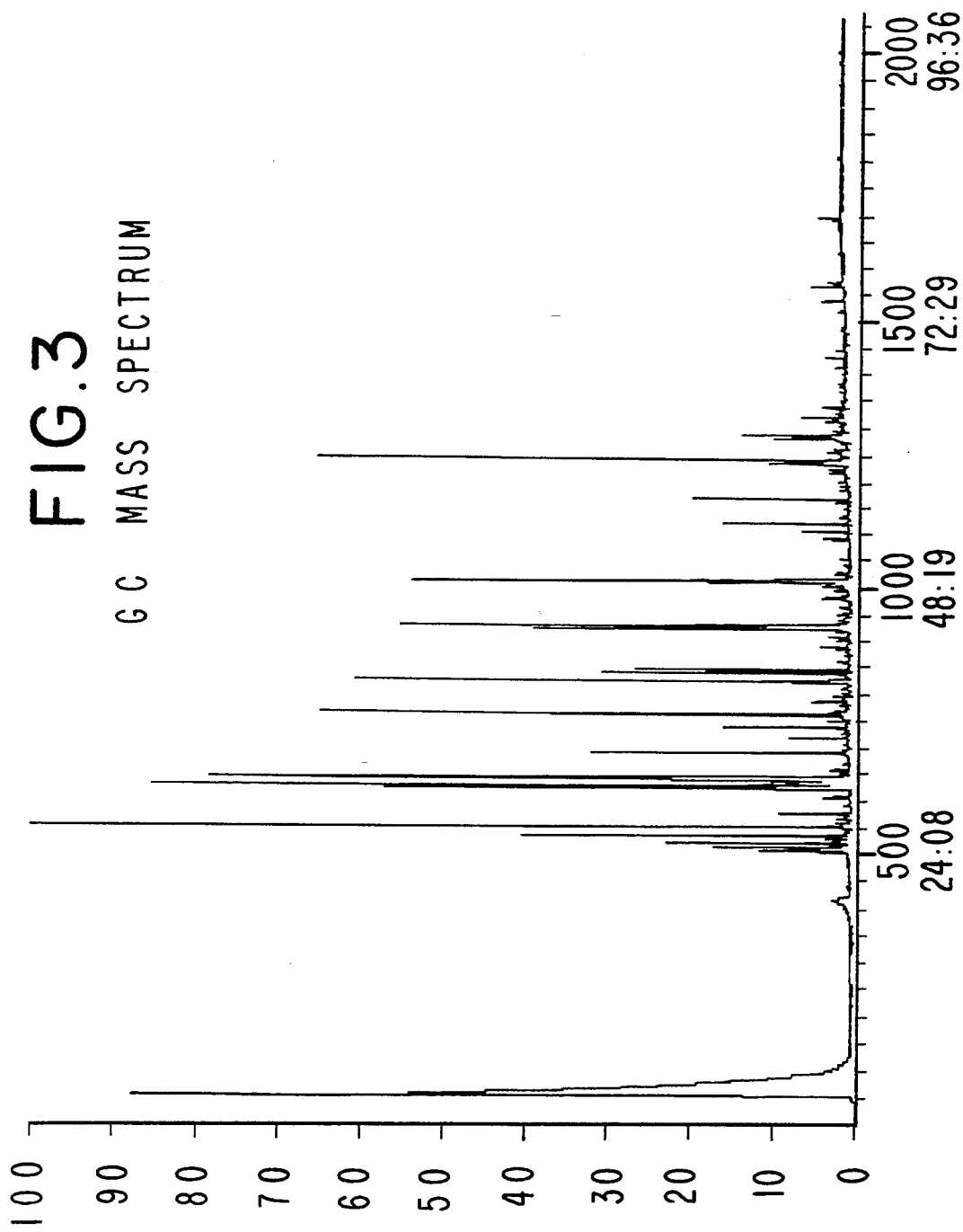
FIG. 3 is a GC-mass spectrum for the aroma components evolved from white *Jasminum nitidum* alone when using the apparatus of FIG. 1B, according to Example I.
Figure 4:
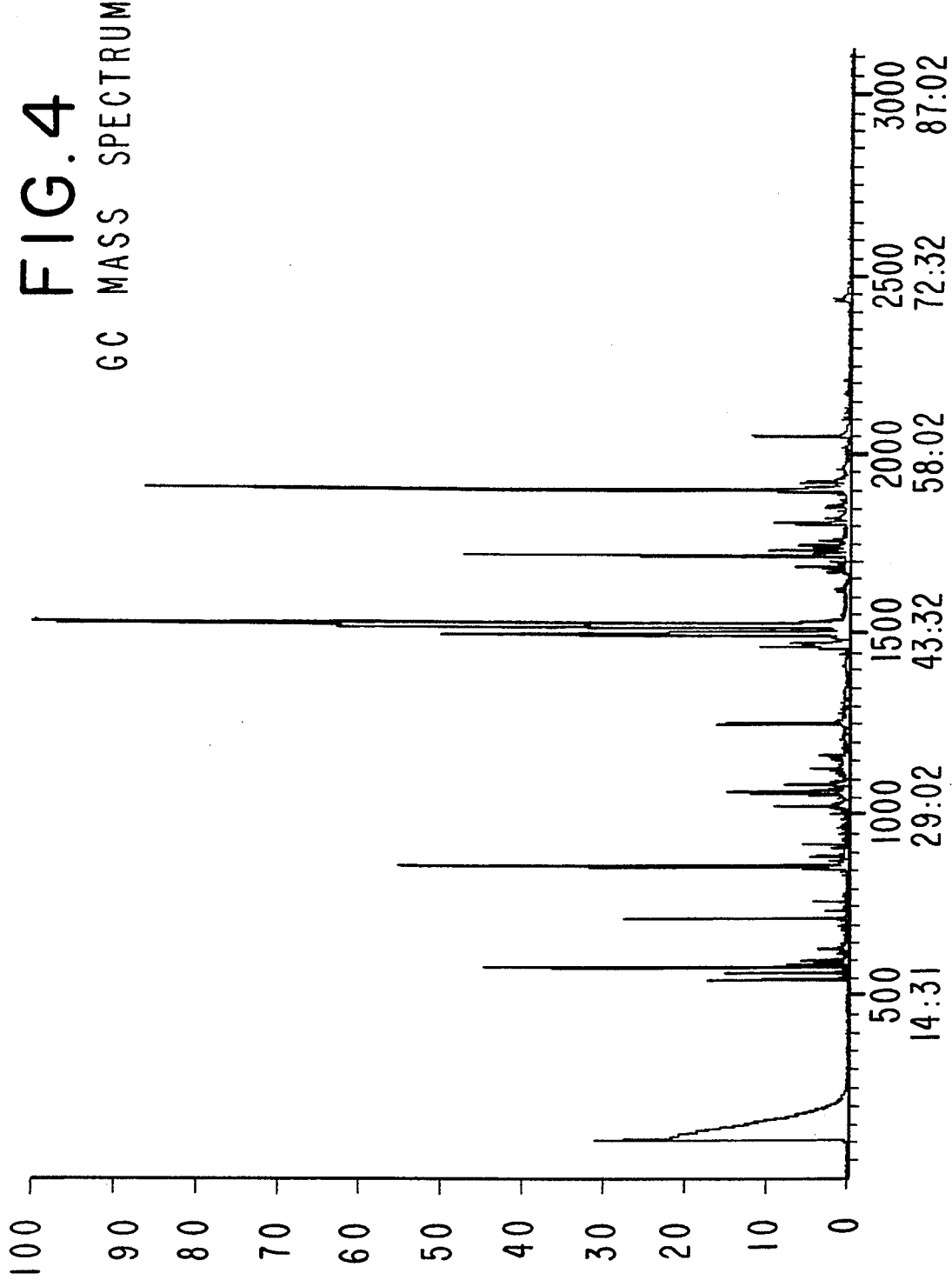
FIG. 4 is the GC-mass spectrum for the aroma components evolved from peach colored rose fragrant delight alone when using the apparatus of FIG. 1B in accordance with Example I.

FIG. 3 is a GC-mass spectrum for the aroma components evolved from white jasminum nitidum alone when using the apparatus of FIG. 1B, according to Example I. The peaks thereon (not indicated with reference numerals) are identified in Table I, infrared of said Example I. FIG. 4 is the GC-mass spectrum for the aroma components evolved from peach colored rose fragrant delight alone when using the apparatus of FIG. 1B in accordance with Example I. The peaks thereon (not indicated with reference numerals) are identified in Table I, infra of said Example I.

Figure 5:
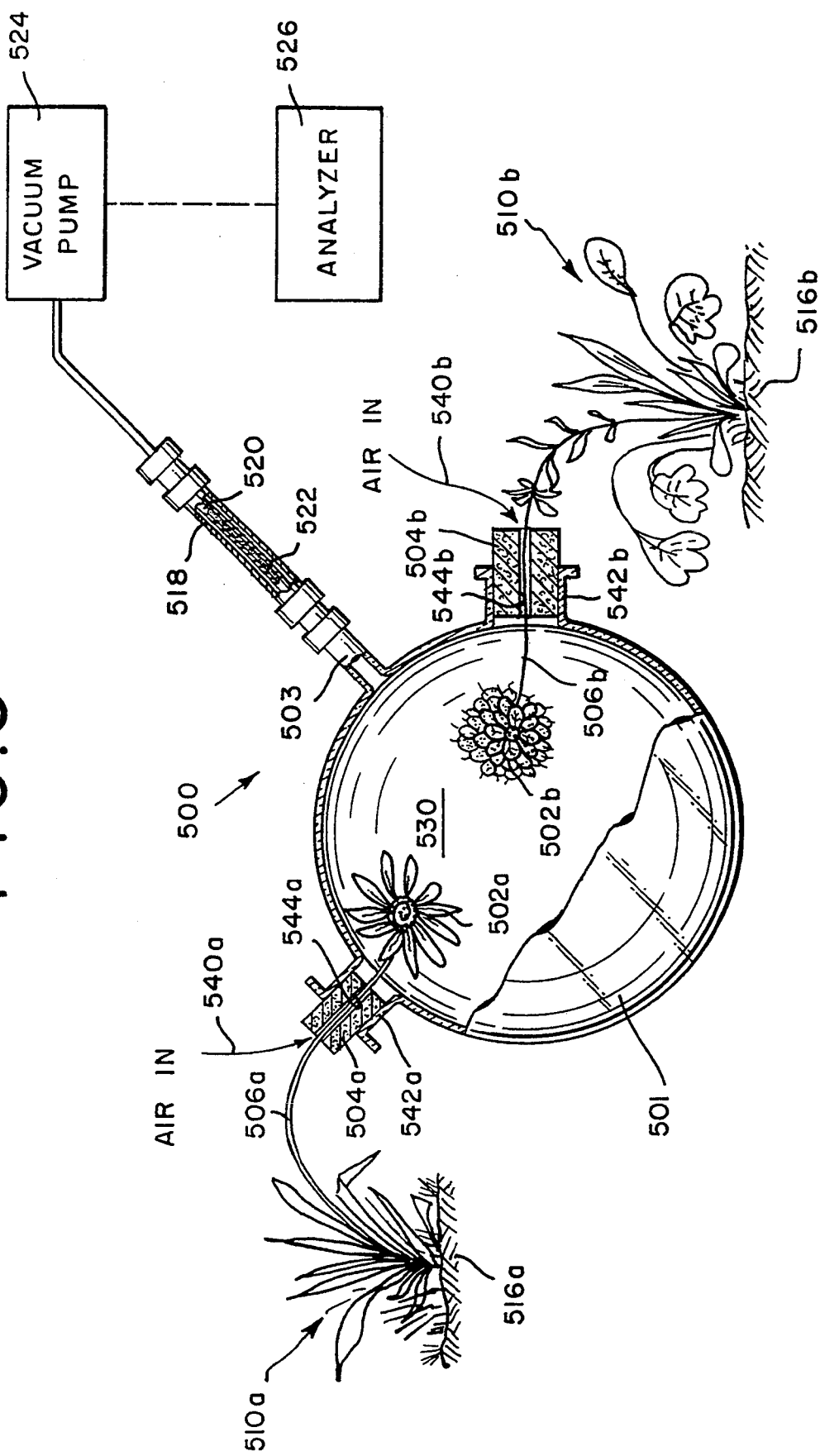
FIG. 5 is a partially cut-away side elevation view of another embodiment of the apparatus of our invention wherein the totally enclosed 3-space is spherical in shape and contained within the totally enclosed 3-space are two different species of living flowers.

In FIG. 5, rather than being bifurcated as in the apparatus of FIG. 1, the apparatus of FIG. 5 has a totally enclosed 3-space in the form of a sphere fabricated from a rigid transparent solid such as glass or polymethyl methacrylate. Flowers 502a and 502b are contained within the totally enclosed 3-space 530. Flower 502b has stem 506b which is held in place by packing 504b held in neck 542b. The stem passes through opening 544b and is part of plant 510b which is growing in the ground 516b similarly plant 510a growing in ground 516a has stem 506a connected to flower 502a. The stem 506a is held in place by packing 504a (packing material) held firmly in place in neck 542a. The stem 506a traverses opening 544a in neck 542a. Tube 503, is the third orifice of the totally enclosed 3-space of apparatus 500. Tube 503 is connected via SWAGELOK® fittings (SWAGELOK® is a trademark of the Swagelok Company of Solon, Ohio 44139) to TENAX® trap 518-520-522. 518 Is the reference numeral showing the outer tube of the TENAX® trap; 522 is the TENAX® packing (e.g., TENAX®-GC); and the inner tube is indicated by reference numeral 520. When vacuum pump 524 is engaged, the aroma components of flowers 502a and 502b pass into the headspace 530 and then through tube 503 into TENAX® packing 522. At the end of the experiment, the TENAX® packing 522 is removed from tube 520 and analyzed using analyzer 526. During the operation of the vacuum pump 524, air 540b and 540a traverses passages 544b and 544a, respectively and picks up the aroma components in headspace 530.

Figure 6:
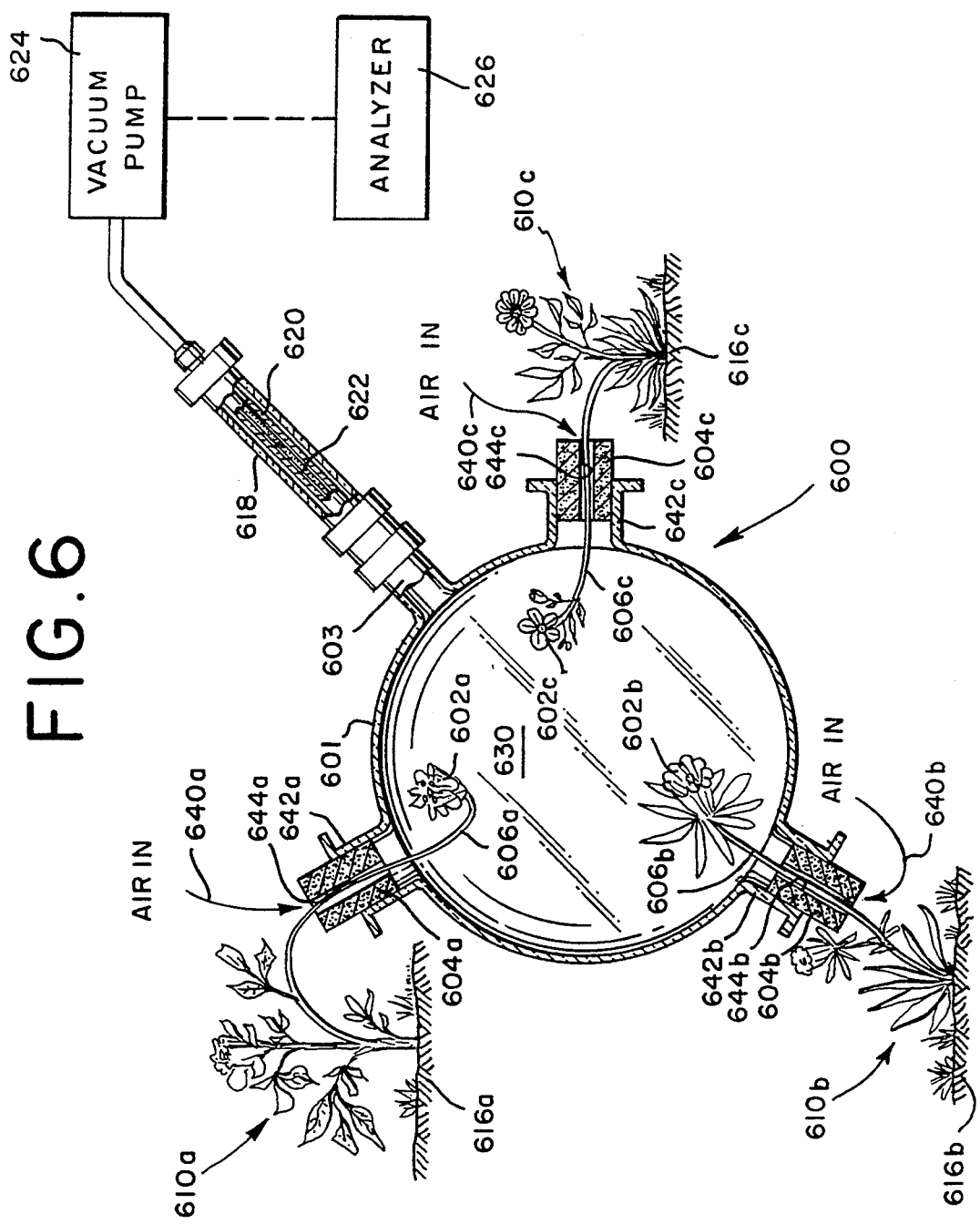
FIG. 6 sets forth another embodiment of the apparatus of our invention in cut-away side elevation view wherein the totally enclosed 3-space is spherical in shape and contained within the totally enclosed 3-space are three different species of living flowers.

FIG. 6 illustrates another embodiment of the apparatus of our invention wherein the totally enclosed 3-space 630 is enclosed by transparent sphere 601 having four orifices. Three flowers, 602a, 602b and 602c are held in place using their stems, respectively, 606a, 606b and 606c at necks 642a, 642b and 642c using packings 604a, 604b and 604c, respectively. The flowers 602a, 602b and 602c have stems, respectively, 606a, 606b and 606c. Each of the stems 606a, 606b and 606c are held in place in necks 642a, 642b and 642c by packings 604a, 604b and 604c. Each of stems 606a, 606b and 606c traverses openings 644a, 644b and 644c, respectively. Each of the stems 606a, 606b and 606c is connected, respectively, to plants 610a, 610b and 610c. The plants respectively being in the grounds 616a, 616b and 616c. When the apparatus 600 is in use, the vacuum pump 624 is engaged and air 640a, 640b and 640c traverses openings 644a, 644b and 644c and travels into the headspace 630 picking up the aroma components of flowers 602a, 602b and 602c and passes these components through orifice 603c connected by SWAGELOK® fittings to TENAX® tube 618 containing inner tube 620 and TENAX® packing (e.g., TENAX®-GC). The aroma components are held on the TENAX® packing until the vacuum pump is disengaged. When the vacuum pump is disengaged, the aroma components are removed from the TENAX® packing as by extraction and analyzed using GC-mass spectral analysis equipment (analyzer 626). Analyzer 626 may also include infrared analytical equipment, ultraviolet analytical equipment, and Raman spectral analytical equipment as well as nuclear magnetic resonance analytical equipment.

Figure 7:
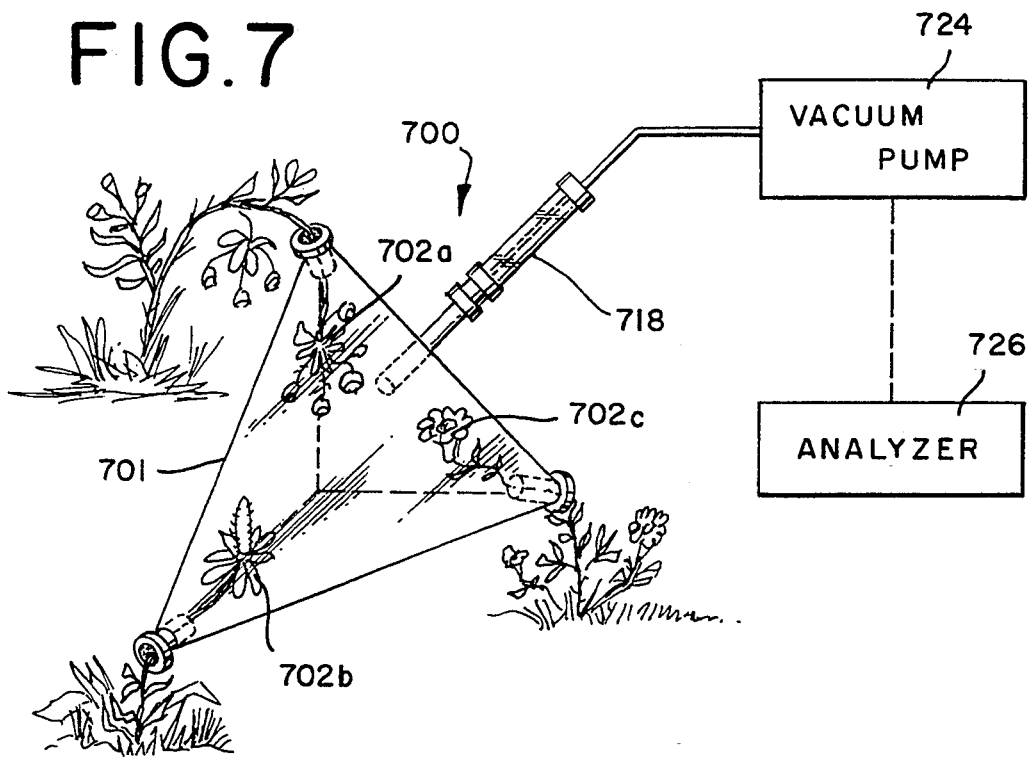
FIG. 7 is a schematic perspective diagram of another embodiment of our invention wherein the totally enclosed 3-space is a tetrahedron and contained within the tetrahedron are three different species of living flowers.

FIG. 7 represents still another embodiment of the apparatus of our invention. The totally enclosed 3-space in this case is a tetrahedron 701 containing flowers 702a, 702b and 702c. The apparatus is indicated by reference numeral 700. When vacuum pump 724 is engaged the aroma components are trapped in a packing contained within tube 718. When the vacuum pump is disengaged, the packing is removed from 718 and analyzed using analyzer 726.

Figure 8:
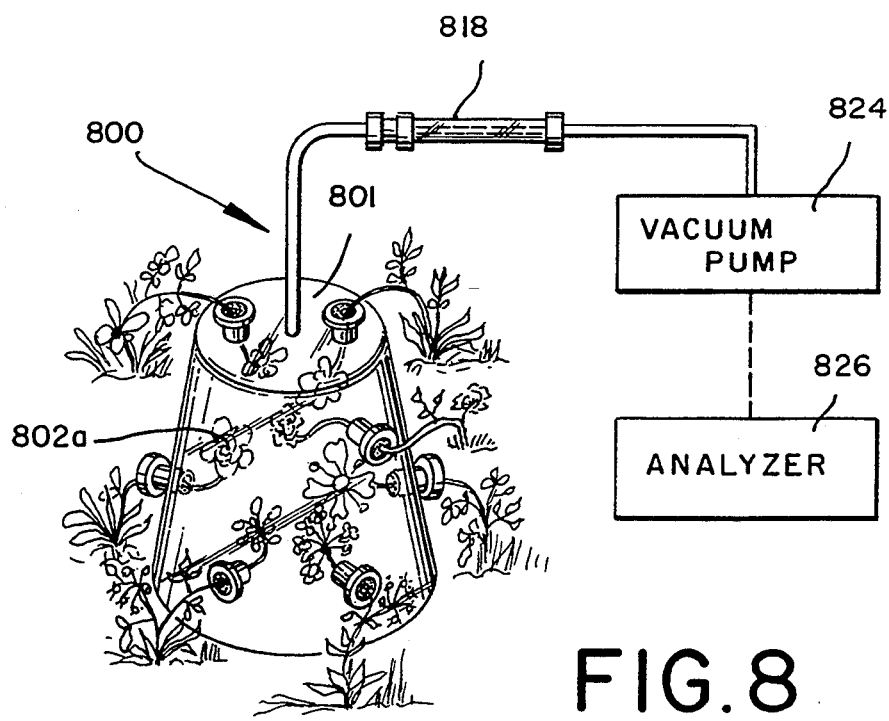
FIG. 8 is a schematic perspective view diagram of another embodiment of the apparatus of our invention wherein the totally enclosed 3-space is a frustum of a right circular cone and the totally enclosed 3-space contains six living flowers of three different species.

FIG. 8 sets forth still another embodiment of our invention showing the totally enclosed 3-space as a frustum of a right circular cone. The apparatus is indicated by reference numeral 800 and the frustum of the right circular cone is indicated by reference numeral 801. The flowers are generally indicated by reference numeral 802. When the vacuum pump 824 is engaged, the headspace components are trapped in trapping material included in tube 818. When the vacuum pump is disengaged, the packing material is removed from tube 818 and analyzed using analyzer 826.

Figure 9:
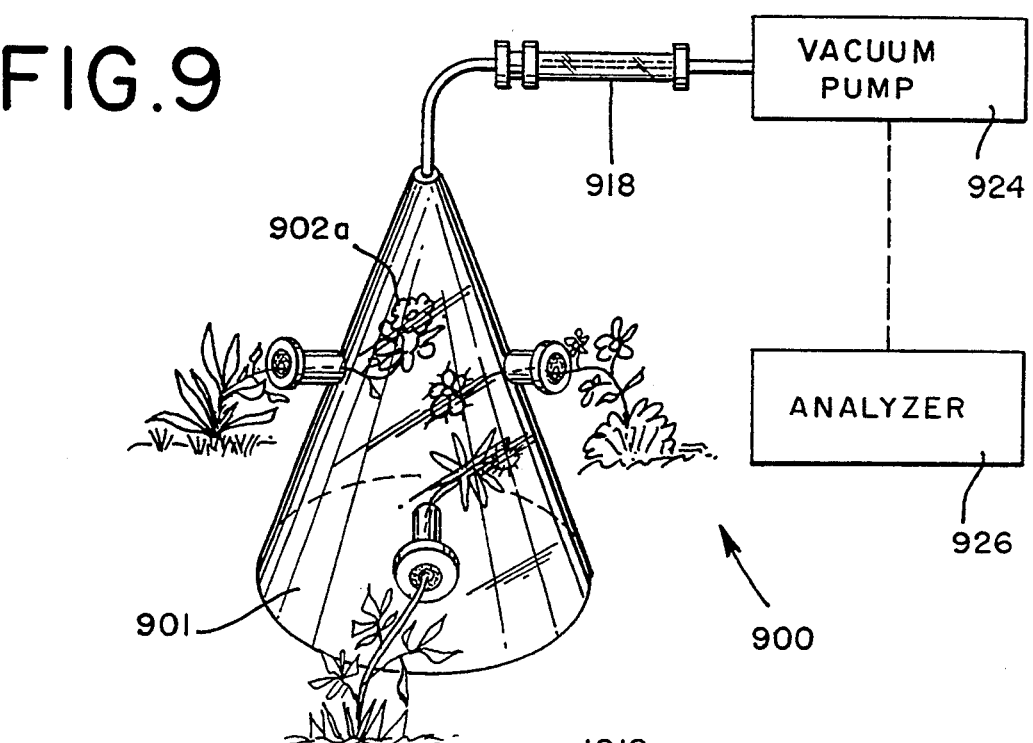
FIG. 9 is a schematic diagram showing in perspective another embodiment of the apparatus of our invention wherein the totally enclosed 3-space is a right circular cone and contained in the right circular cone are three different species of living flowers.

FIG. 9 is still another embodiment of the apparatus of our invention wherein the totally enclosed 3-space is in the shape of a right circular cone 901. The apparatus is indicated by reference numeral 900. The flowers are indicated by reference numeral 902 (e.g., 902a). When the vacuum pump 924 is engaged the aroma components from the flowers headspace 902 are trapped in packing contained in tube 918. When the vacuum pump is disengaged the packing is removed from tube 918 and extracted and analyzed using analyzer 926.

Figure 10:
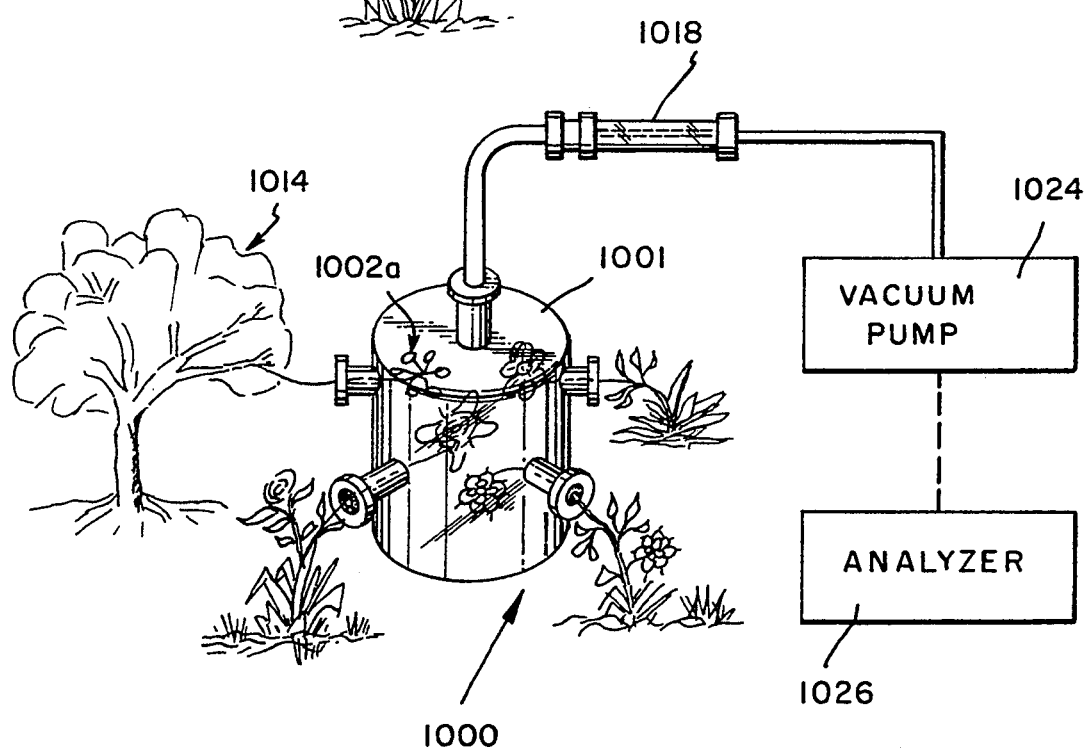
FIG. 10 is a schematic perspective diagram of another embodiment of the apparatus of our invention wherein the totally enclosed 3-space is in the shape of a right circular cylinder and contained within the right circular cylinder are four different species of living flowers; three species from three plants and a fourth species from the branch of a living tree.

FIG. 10 illustrates another embodiment of the apparatus of our invention wherein the totally enclosed 3-space is a right circular cylinder 1001. The apparatus is indicated by reference numeral 1000. The flowers are indicated by reference numeral 1002 (for example, 1002a). The flowers may be either connected to living plants or a living tree 1014. When vacuum pump 1024 is engaged, the components of the headspace 1001 are trapped in packing contained in tube 1018. When the vacuum pump 1024 is disengaged, the packing is removed from tube 1018 and analyzed using analyzer 1026.

Figure 11:
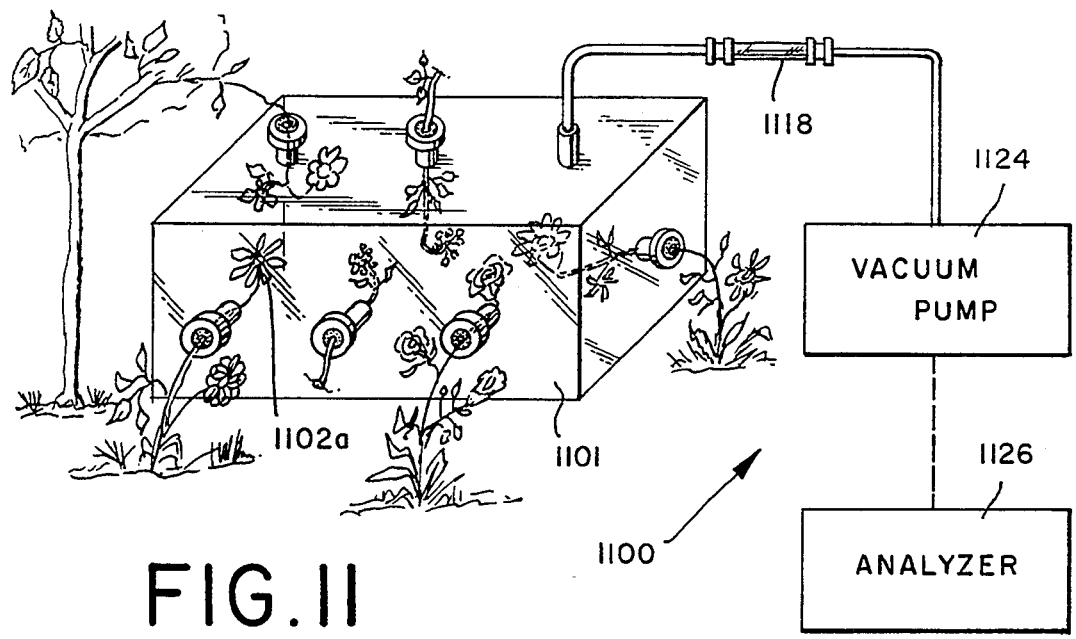
FIG. 11 is a schematic perspective diagram of another embodiment of the apparatus of our invention wherein the single totally enclosed 3-space is a rectangular parallelapiped and enclosed within the rectangular parallelapiped are five different species of living flowers; four species from plants and a fifth species from a living tree.

FIG. 11 illustrates still another embodiment of the apparatus of our invention. The totally enclosed 3-space is a rectangular parallelapiped indicated by reference numeral 1101. Living flowers are contained in the rectangular parallelapiped 1101 indicated by reference numeral 1102 (for example, 1102a). When vacuum pump 1124 is engaged, the aroma components contained in 1101 are trapped in packing contained in tube 1118.

When vacuum pump 1124 is disengaged, the packing contained in tube 1118 is removed and extracted and analyzed in analyzer 1126. The overall apparatus is indicated by reference numeral 1100.

Figure 12:
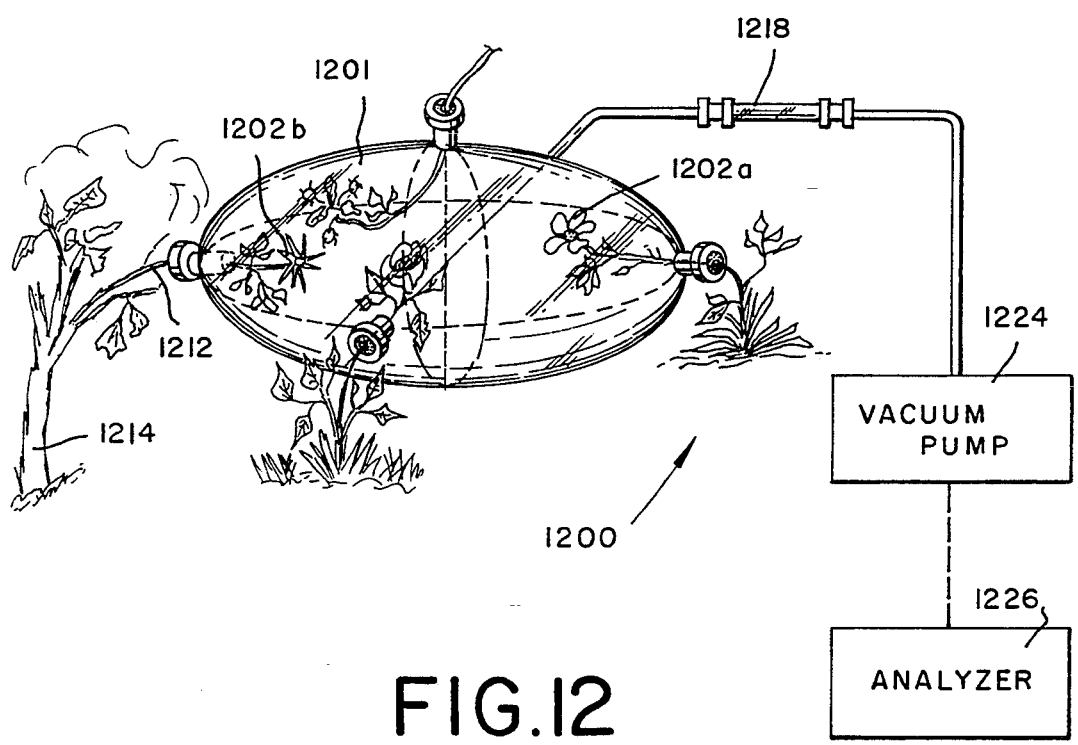
FIG. 12 is a schematic perspective diagram of another embodiment of the apparatus of our invention wherein the single totally enclosed 3-space is in the shape of an ellipsoid and contained within the ellipsoid are four different species of living flowers; three of the living flowers from living plants and a fourth of the living flowers from a branch of a living tree.
Figure 20:
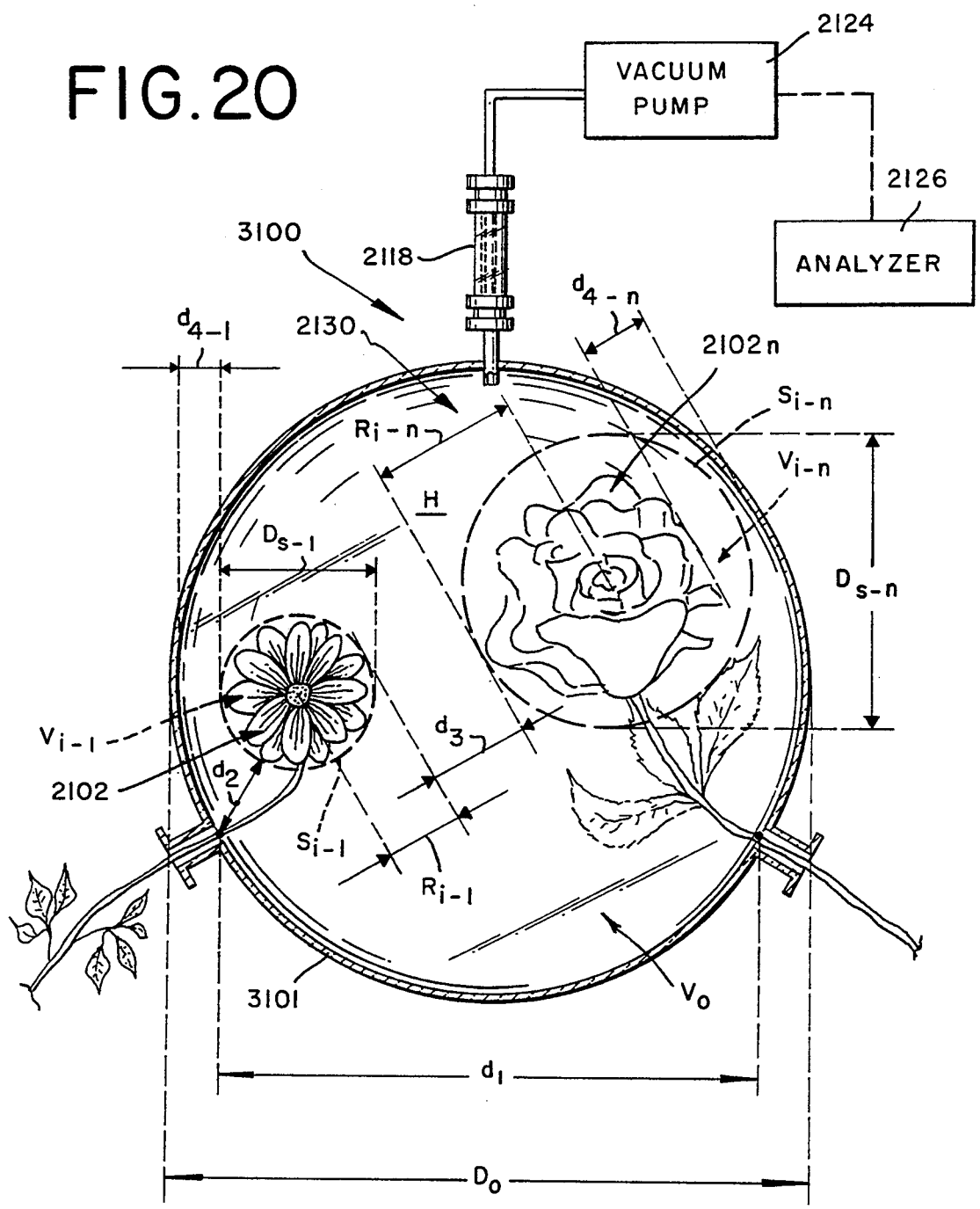
FIG. 20 is a schematic cut-away side elevation view of an embodiment of the apparatus of our invention showing in schematic form the single totally enclosed 3-space containing two living flowers with indications as to the surfaces $S_{i\text{-}n}$ which are mathematically constructed as spheres around the largest petal of the living flower with the volumes of the mathematically constructed spheres being shown to have volumes $V_{i\text{-}n}$ and with the distances $d_1$, $d_2$, $d_3$ and $d_4$ indicated.

FIG. 12 illustrates still another embodiment of the apparatus of our invention wherein the totally enclosed 3-space is an ellipsoid 1201. The overall apparatus is indicated by reference numeral 1200. The living flowers contained in the ellipsoid are indicated by reference numeral 1202 (for example, 1202a and 1202b). Flower 1202b is connected via stem 1212 to tree 1214. When vacuum pump 1224 is engaged, the aroma components in the headspace of ellipsoid 1201 are drawn into packing contained in tube 1218. When the vacuum pump 1224 is disengaged, the packing is removed from tube 1218, extracted and the extract is analyzed using analyzer 1226.

FIGS. 13 and 14 illustrate additional embodiments of the apparatus of our invention wherein the totally enclosed 3-space contains baffles which impart turbulence to the flow of air when the vacuum pumps 1324 and 1424 are engaged.

Thus, more specifically, FIG. 13 shows the totally enclosed 3-space as being an ellipsoid 1301 having baffles connected to the inner wall of the ellipsoid, the baffles being indicated by reference numeral 1319. The overall apparatus is indicated by reference numeral 1300. When vacuum pump 1324 is engaged, the aroma components in the headspace of ellipsoid 1301 are drawn into packing (e.g., TENAX ®-GC) contained in tube 1318. When the vacuum pump 1324 is disengaged, the TENAX ® packing is removed from tube 1318, extracted and analyzed using analyzer 1326.

Referring specifically to FIG. 14, FIG. 14 shows the totally enclosed 3-space as being a right circular cone 1401 having baffles contained and connected to the inner wall thereof, said baffles being indicated by reference numeral 1419. When vacuum pump 1424 is engaged, the aroma components contained in cone 1401 in the headspace thereof are drawn into packing contained in tube 1418. When the vacuum pump 1424 is disengaged, the packing from tube 1418 is removed from tube 1418, extracted and analyzed in analyzer 1426. The overall apparatus is indicated by reference numeral 1400. FIG. 15 is the GC-mass spectrum for the analysis of the biflower which is the subject of the analysis and fragrance formulation of Example II. The two flowers used are the Yellow Osmanthus Olive and the Peach Rose Fragrant Delight. The group of peaks indicated by reference numeral 50 is the "background". The peak indicated by reference numeral 51 is for benzaldehyde. The peak indicated by reference numeral 52 is for 6-methyl-5-hepten-2-one. The peak indicated by reference numeral 53 is for cis-3-hexenyl acetate. The peak indicated by reference numeral 49 is for hexyl acetate. The peak indicated by reference numeral 54 is for trans-beta-ocimene. The peak indicated by reference numeral 48 is for linalool. The peak indicated by reference numeral 55 is for beta-phenylethyl alcohol. The peak indicated by reference numeral 56 is for 4,8-dimethyl-1,3,7-nonotriene. The peak indicated by reference numeral 57 is for nerol. The peak indicated by reference numeral 58 is for beta-phenylethyl acetate. The peak indicated by reference numeral 59 is for geraniol. The peak indicated by reference numeral 60 is for 3,5-dimethoxy toluene. The peak indicated by reference numeral 61 is for geranyl acetate. The peak indicated by reference numeral 62 is for dihydro-alpha-ionone. The peak indicated by reference numeral 63 is for alpha-ionone. The peak indicated by reference numeral 64 is for dihydro-beta-ionol. The peak indicated by reference numeral 47 is for dihydro-beta-ionone. The peak indicated by reference numeral 65 is for beta-ionone. The peak indicated by reference numeral 66 is for, germacrene-D. The peak indicated by reference numeral 67 is for a heptadecene isomer. The peak indicated by reference numeral 68 is for n-heptadecane. The peak indicated by reference numeral 69 is for a nonadecene isomer.

FIG. 16 is the GC-mass spectrum for the analysis of the headspace of the product produced according to Example III wherein the biflower contained in the apparatus of FIGS. 1A and 1B is Ginger Lily Flower and *Jasminum odoratissimum* Flower.

The peaks indicated by reference numeral 70 are for the "background". The peak indicated by reference numeral 71 is for cis-3-hexenyl acetate. The peak indicated by reference numeral 72 is for trans-2-hexenyl acetate. The peak indicated by reference numeral 73 is for trans-beta-ocimene. The peak indicated by reference numeral 74 is for methyl benzoate. The peak indicated by reference numeral 75 is for linalool. The peak indicated by reference numeral 76 is for 4,8-dimethyl-1,3,7-nonatriene. The peak indicated by reference numeral 77 is for benzyl acetate. The peak indicated by reference numeral 78 is for cis-3-hexenyl butyrate. The peak indicated by reference numeral 79 is for methyl salicylate. The peak indicated by reference numeral 80 is for phenylethyl acetate. The peak indicated by reference numeral 81 is for germacrene-D.

FIG. 17 is the GC-mass spectrum for the analysis of the headspace created as a result of carrying out the procedure of Example IV wherein the biflower contained in the totally enclosed 3-space of FIGS. 1A and 1B is Purple *Heliotropium iowa* and *Jasminum odoratissimum* Flower.

The peaks indicated by reference numeral 82 are for the "background". The peak indicated by reference numeral 83 is for cis-3-hexenol. The peak indicated by reference numeral 84 is for trans-2-hexenol. The peak indicated by reference numeral 85 is for benzaldehyde. The peak indicated by reference numeral 86 is for cis-3-hexenyl acetate. The peak indicated by reference numeral 87 is for trans-2-hexenyl acetate. The peak indicated by reference numeral 88 is for benzyl alcohol. The peak indicated by reference numeral 89 is for methyl benzoate. The peak indicated by reference numeral 90 is for linalool. The peak indicated by reference numeral 91 is for benzyl acetate. The peak indicated by reference numeral 92 is for methyl salicylate. The peak indicated by reference numeral 93 is for anisic aldehyde. The peak indicated by reference numeral 94 is for phenylethyl acetate. The peak indicated by reference numeral 95 is for indole. The peak indicated by reference numeral 96 is for alpha-farnesene. The peak indicated by reference numeral 97 is for benzyl cyanide.

FIG. 18 is the GC-mass spectrum for the analysis of the headspace over the biflower Dwarf Navel Orange Flower taken together with *Jasmin nitidum* Flower produced according to the procedure of Example V, infra.

The peaks indicated by reference numeral 970 is for the "background". The peak indicated by reference numeral 98 is for 2-cyanobutane. The peak indicated by reference numeral 99 is for myrcene. The peak indicated by reference numeral 100 is for benzyl alcohol. The peak indicated by reference numeral 101 is for limonene. The peak indicated by reference numeral 102 is for trans-beta-ocimene. The peak indicated by reference numeral 103 is for methyl benzoate. The peak indicated by reference numeral 104 is for linalool. The peak indicated by reference numeral 105 is for beta-phenylethyl alcohol. The peak indicated by reference numeral 106 is for methyl salicylate. The peak indicated by reference numeral 107 is for methyl anthranilate. The peak indicated by reference numeral 108 is for cis-jasmone. The peak indicated by reference numeral 109 is for beta-caryophyllene. The peak indicated by reference numeral 110 is for beta-selinene. The peak indicated by reference numeral 111 is for alpha-farnesene.

FIG. 19 is the GC-mass spectrum for the analysis of the headspace obtained by carrying out the procedure of Example VI wherein two flowers are contained in the totally enclosed 3-space in the apparatus of FIGS. 1A and 2B, to wit: (i) Red Rose All That Jazz and (ii) White Ginger Lily Flower. The peak indicated by reference numeral 112 is for 3-methyl butyronitrile. The peak indicated by reference numeral 113 is for an isomer of 2-pentenal. The peak indicated by reference numeral 114 is for pentanal oxime. The peak indicated by reference numeral 115 is for 2,5-dihydro-3-methyl furan. The peak indicated by reference numeral 116 s for myrcene. The peak indicated by reference numeral 117 is for limonene. The peak indicated by reference numeral 118 is for cis-ocimene. The peak indicated by reference numeral 119 is for trans-ocimene. The peak indicated by reference numeral 120 is for methyl benzoate. The peak indicated by reference numeral 121 is for linalool. The peak indicated by reference numeral 122 is for 4,8-dimethyl-1,3,7-nonatriene. The peak indicated by reference numeral 123 is for 3,5-dimethoxy toluene. The peak indicated by reference numeral 124 is for cis jasmone. The peak indicated by reference numeral 125 is for germacrene-D. The peak indicated by reference numeral 126 is for farnesene. The peak indicated by reference numeral 127 is for 1-nonadecene.

Figure 21:
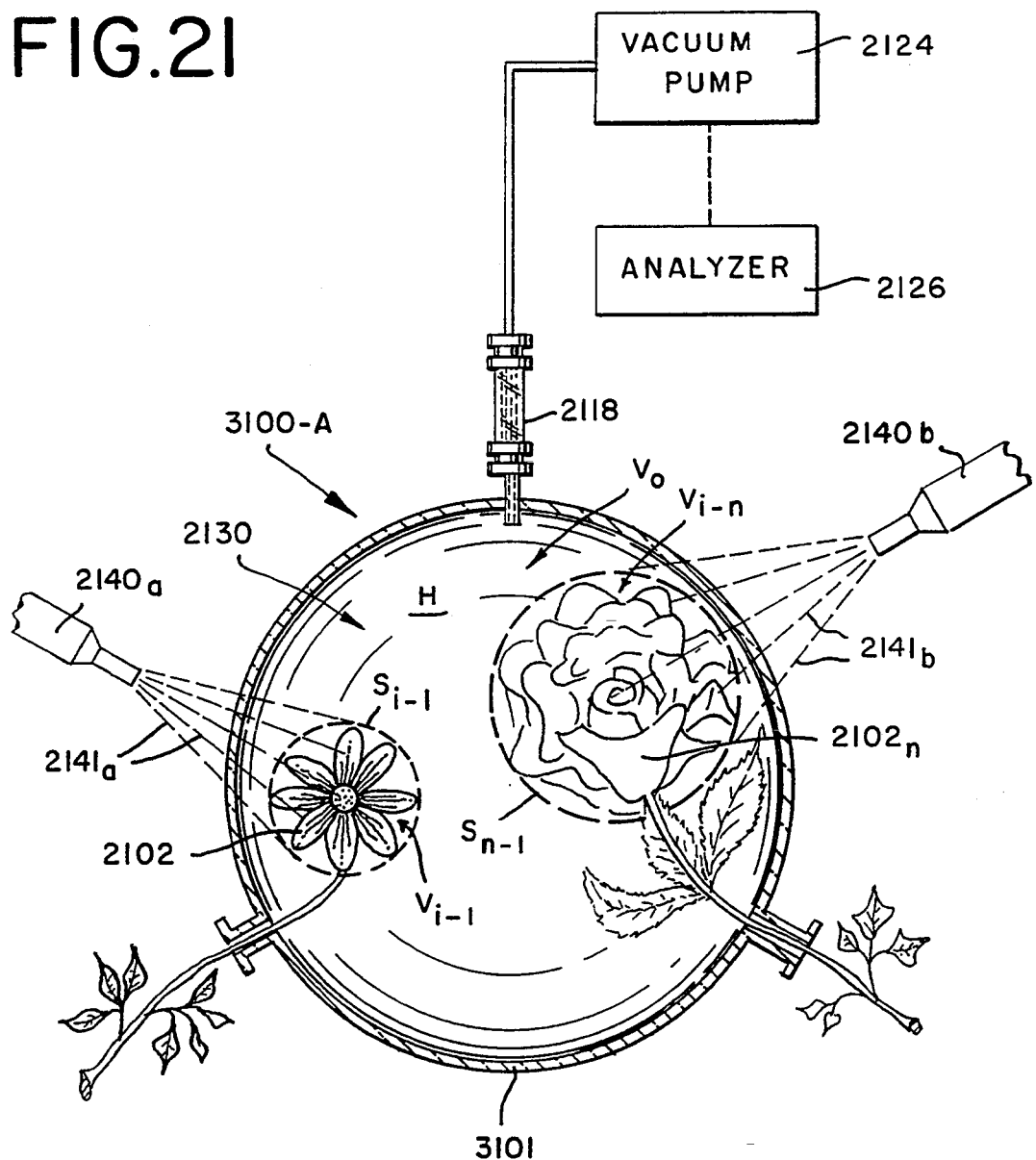
FIG. 21 is another embodiment of the apparatus of FIG. 20 showing the use of ultraviolet sources emitting ultraviolet radiation onto each of the living flowers contained within the totally enclosed 3-space.
Figure 22:
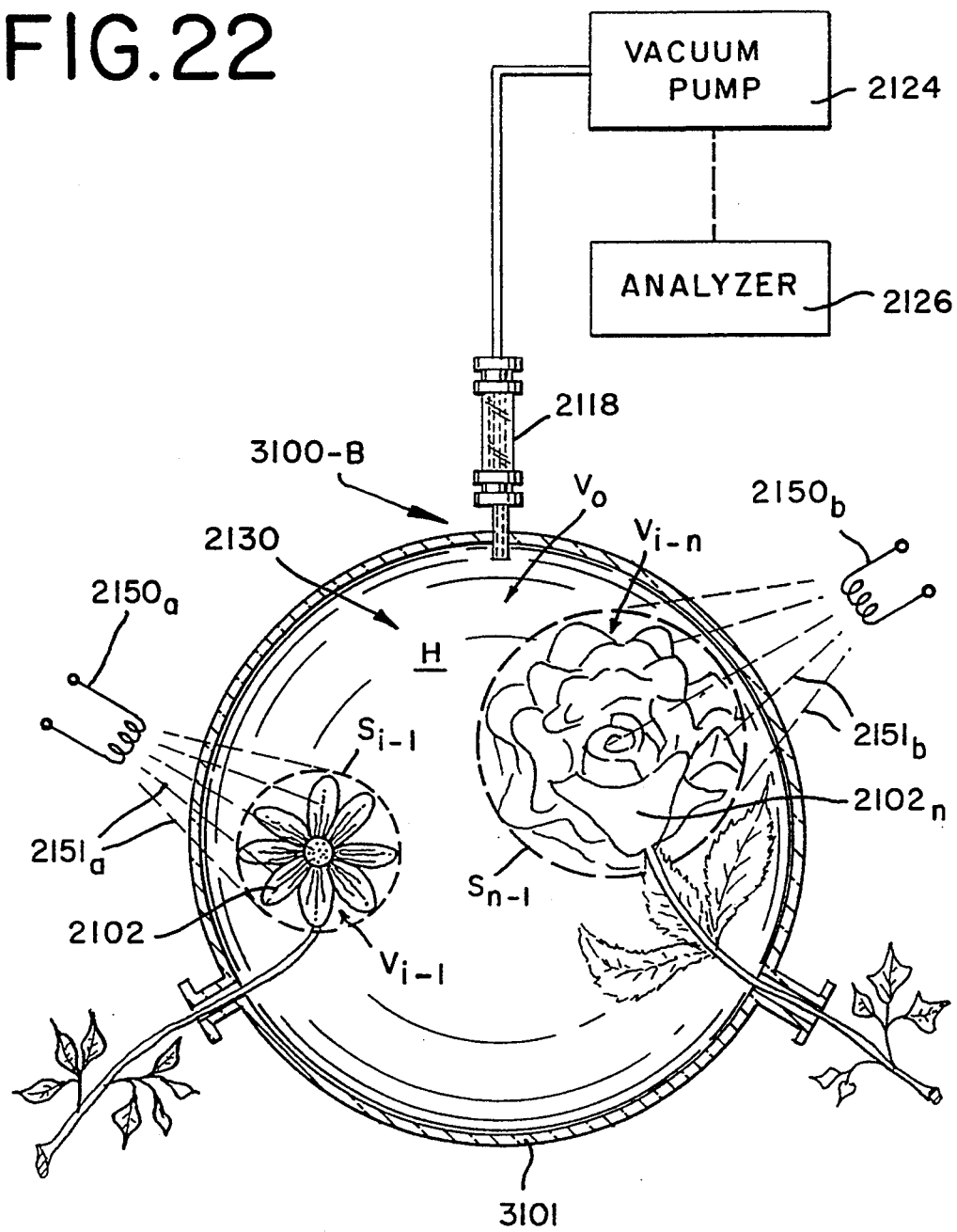
FIG. 22 is another embodiment of the apparatus of FIG. 20 showing the use of infrared radiation sources emitting infrared radiation onto the living flowers contained within the totally enclosed 3-space.
Figure 23:
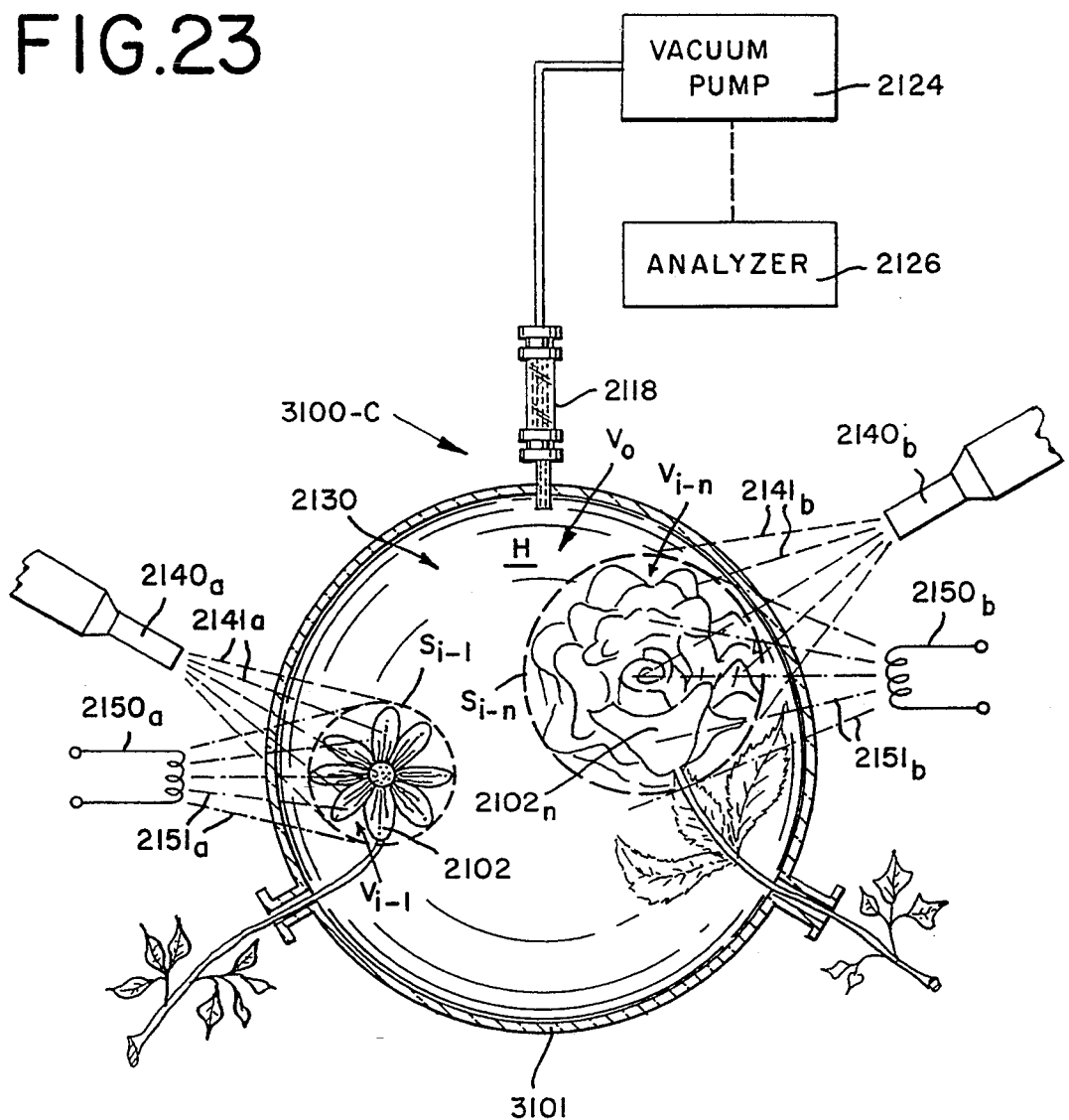
FIG. 23 is another embodiment of the apparatus of FIG. 20 showing the use of both ultraviolet sources and infrared sources emitting, respectively, ultraviolet radiation and infrared radiation onto the living flowers contained in the totally enclosed 3-space.

FIGS. 20, 21, 22 and 23 show schematic cut-away diagrams of the apparatus of our invention indicating the location of various mathematical terms Flowers 2102 and 2102n are located within headspace 2130 contained in spherical enclosure 3101. The entire apparatus is indicated by reference numeral 3100 (for FIG. 20), 3100A (for FIG. 21), 3100B (for FIG. 22) and 3100C (for FIG. 23). When vacuum pump 2124 is engaged, headspace components are drawn into a packing contained in tube 2118. When the vacuum pump 2124 is disengaged, the packing is removed from tube 2118 and analyzed in analyzer 2126. The diameter of the totally enclosed 3-space is indicated by $D_0$. The diameter of a mathematically constructed sphere around the longest petal of each flower is indicated by the terms $D_{i\text{-}1}$ and $D_{i\text{-}n}$. The radii for such mathematically constructed spheres are indicated by the terms $R_{i\text{-}1}$ and $R_{i\text{-}n}$. The volumes of the mathematically constructed spheres are indicated by the terms $V_{i\text{-}1}$ and $V_{i\text{-}n}$ and the surfaces of the mathematically constructed spheres are indicated by $S_{i\text{-}1}$ and $S_{i\text{-}n}$. The distance from the mathematically constructed sphere to the inner side of the totally enclosed 3-space is indicated by $d_4$ and $d_{4\text{-}n}$. The distance between the mathematically constructed spheres representing the flowers which are the living flowers is indicated by $d_3$ and the distance from the mathematically constructed sphere which are the living flowers to each orifice is indicated by $d_2$. The distance between the orifices which hold the stems of the flowers 2102 and 2102n in place is indicated by $d_1$. The volume of the overall headspace (without taking into account the headspace of the mathematically constructed spheres) is indicated by $V_0$. In FIG. 21 a UV source 2140a and 2140b is shown emitting radiation 2140a and 2140b onto flowers 2102 and 2102n respectively. The radiation is ultraviolet radiation 2141a and ultraviolet radiation 2141b from ultraviolet sources 2140a and 2140b respectively. In FIG. 22 the radiation source 2150a is an infrared radiation source emitting infrared radiation 2151a onto flower 2102 and radiation 2151b onto flower 2102n from radiation source 2150b. In FIG. 23 the radiation sources are two in number for each flower; ultraviolet radiation source 2140a emitting ultraviolet radiation 2141a; infrared radiation source 2150a emitting infrared radiation 2151a all onto flower 2102. Ultraviolet radiation source 2140b emits ultraviolet radiation 2141b onto flower 2102n and infrared radiation source 2150b emits infrared radiation 2151b onto flower 2102n (that is, the mathematically constructed flower).

Figures 24, 25:
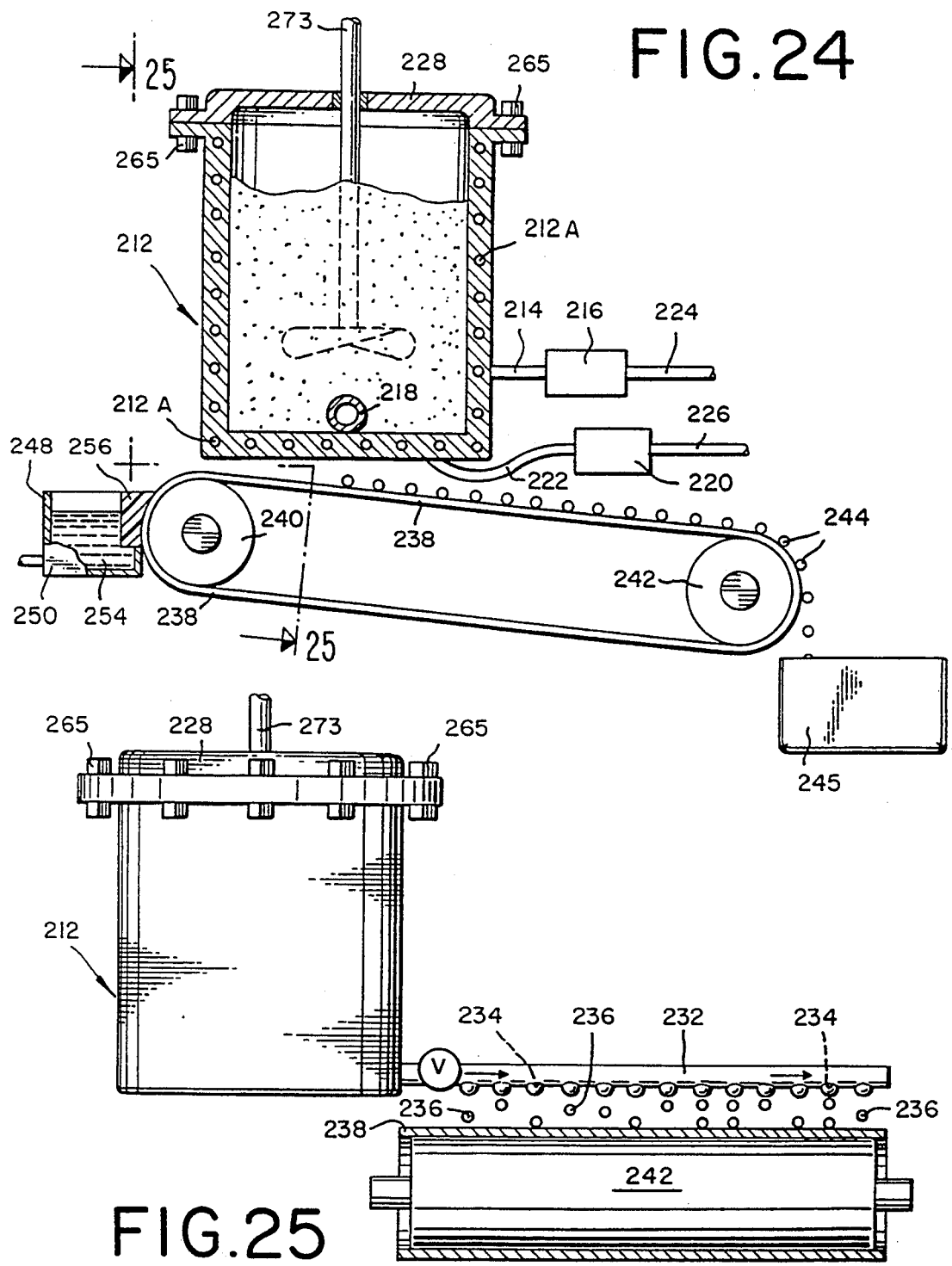
FIG. 24 represents a cut-away side elevation view of apparatus used in forming perfumed polymers containing at least one of the living flower compositions of our invention.
FIG. 25 is a front view of the apparatus of FIG. 24 looking in the direction of the arrows.

Referring to FIGS. 24 and 25, there is provided a process for forming scented polymer pellets (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material of the container is taken off at such location for delivery through the conduit. Thus, referring to FIGS. 24 and 25, in particular, the apparatus used in producing such elements comprises a device for forming the polymer containing perfume, e.g., polyethylene or polyethylene-polyvinyl acetate or mixtures of same or polypropylene, or the like, which comprises a vat or container 212 into which the polymer taken alone or in admixture with other copolymers and a perfuming substance containing at least one of the living flower fragrances of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212A having heated coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds.

Heating means (coils 212A) are operated to maintain the upper portion of the container 212 within a temperature range of, for example, 250°–260° C. in the case of low density polyethylene. The bottom portion of the container 212 is also heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing at least one of the living flower fragrances of our invention is quickly added to the melt. Generally, about 10–45 percent by weight of the resulting mixture of the perfumery substance is added to the polymer.

After the perfume material containing at least one of the living flower fragrances of our invention is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also indicated by reference numeral 218 in FIG. 24) having a multiplicity of orifices 234 adjacent to the lower side thereof. The outer end of the conduit 232 is closed so that the liquid polymer intimately admixed with at least one of the living flower fragrances of our invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the living flower fragrances of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

The following examples are illustrative of processes for using the apparatus of our invention, processes for carrying out production of fragrance formulations of our invention and processes for using the living flower fragrances of our invention. These examples are illustrative and the invention is to be considered to be restricted thereto only as indicated in the appended claims.

All parts and percentages given herein are by weight unless otherwise specified.

EXAMPLE I

Headspace Analysis and Fragrance Formulation Produced Therefrom Using *Jasminum nitidum* and Peach Rose Fragrant Delight Apparatus was built as set forth in FIGS. 1A and 1B. The apparatus 2100 consists of two hemispherical shells fabricated from glass, having a shell wall 0.125" in thickness; and a shell diameter of 8". Prior to putting hemispherical walls 2101a and 2101b together, two living growing flowers; *Jasminum nitidum* and peach rose fragrant delight (2106 and 2104 respectively) are placed through openings 2144a and 2144b. Thus, the peach rose fragrant delight flower 2102 having stem 2106 coming out of plant 2110 is pushed through opening 2144a. The *Jasminum nitidum* flower 2104 is pushed through opening 2144b. Flower 2104 is connected through stem 2108 to plant 2112. The two hemispheres are wedged together held in place by clamps 2128.

Pump 2124 is engaged and run for a period of two hours.

The aroma components of the double flower headspace is trapped in a ⅛" diameter×4" long TENAX ®-GC headspace trap further inserted into a glass tube being 5" in length×¼" outer diameter. The pump is an alpha-2 pump (vacuum pump) "a low flow" pump marketed by the Amatec Company of Largo, Fla. 34643 (the amatec constant flow sampler).

The same procedure is repeated on individual flowers; to wit: *Jasminum nitidum* and peach rose fragrant delight. The results of the three analyses are set forth in Table I below:

TABLE I

| Compound Identified | Area % In Rose Fragrant Delight | Area % In Jasmimum Nitidum | Area % Combined Rose/ Jasmine (Rasmine) |
|---|---|---|---|
| Isovaleraldehyde | — | 1.92 | 0.73 |
| 2-Cyanobutane | — | 0.81 | 0.64 |
| 3-Methyl Butyronitrile | — | 5.49 | 1.1 |
| 3-Methyl Butanol | — | — | 0.31 |
| 2-Methyl Butanol | — | — | 0.54 |
| Hexanal | 0.12 | — | — |
| 4-Methyl 3-Penten-2-one | — | — | 0.06 |
| Butyl Acetate | 0.2 | — | — |
| 4-Methyl Pentanenitrile | — | 0.02 | 0.1 |
| 5-Methyl-2-Acetyl Furan | 0.01 | — | — |
| Unknown | — | — | 3.53 |
| Unknown | — | 16.17 | 1.78 |
| Unknown | — | 11.71 | 4.29 |
| Unknown | — | — | 4.06 |
| Isoamyl Acetate | 1.05 | — | 19.54 |
| Cyclohexanone | 8.82 | — | — |
| Cyclohexen,1-Acetate | 0.18 | — | — |
| 2-Hexenyl Acetate | 0.23 | — | 0.44 |
| Amyl acetate | 0.09 | — | 0.22 |
| 2-Buten-1-ol,3-Methyl Acetate | 0.37 | — | 0.34 |
| 2-Butoxy Ethanol | — | 0.04 | — |
| Methyl Anisole | 0.05 | 0.02 | 0.02 |
| 5,5-Dimethyl 2-(5)-Furanone | 0.01 | — | — |
| Benzaldehyde | 0.09 | 2.07 | 0.23 |
| Pentenal Oxime | — | — | 0.01 |
| 1-Pentanol,3-Methyl Acetate | — | — | 1.81 |
| 2-Octanone | 0.01 | — | — |
| Benzyl Methyl Ether | 0.1 | — | 0.45 |
| 5-Hepten-2-ol,6-Methyl | 0.1 | — | 0.51 |
| 5-Hepten-2-one,6-Methyl | 1.21 | 0.65 | 0.7 |
| Phenol | 0.15 | 0.02 | — |
| Myrcene | 1.24 | — | 0.5 |
| Cis-3-Hexenyl Acetate | 1.16 | 1.02 | 1.19 |
| 1-Methyl Pyrrolidone | — | — | 0.01 |
| Hexyl Acetate | 0.68 | — | 1.4 |
| Trans-2-Hexenyl Acetate | 0.14 | — | — |
| Benzyl Alcohol | 0.05 | 10.15 | 0.53 |
| Cyclohexyl Acetate | 0.15 | — | — |
| Limonene | 0.44 | — | 0.14 |
| Indene | — | — | 0.08 |
| Cis-Beta Ocimene | 0.06 | 0.01 | 0.03 |
| 2-Nonen-5-One | — | — | 0.01 |
| 2,6-Octadiene-2,7-Dimethyl | 0.19 | 0.35 | 0.26 |
| Trans-Beta-Ocimene | 0.32 | — | 0.32 |
| Cymene | 0.04 | 0.02 | 0.02 |
| Hydratropic Aldehyde | — | — | 0.02 |
| Linalool Oxide And | — | −.07 | 0.07 |

TABLE I-continued

| Compound Identified | Area % In Rose Fragrant Delight | Area % In Jasmimum Nitidum | Area % Combined Rose/Jasmine (Rasmine) |
|---|---|---|---|
| Isomer 3,5-Heptadiene-2-One, 6-Methyl | — | 0.01 | — |
| Methyl Benzoate | — | 6.4 | 2.3 |
| Phenethyl Alcohol | 1.95 | 2.6 | 1.6 |
| Benzyl Cyanide | — | 2.19 | 0.57 |
| Rose Oxide | 0.03 | — | 0.06 |
| 2-Ethyl Hexanoic Acid | — | 0.03 | — |
| Undecane | — | — | 0.06 |
| 4,8-Dimethyll,3,7,-Nonatriene | 0.1 | — | 2.0 |
| Rose Oxide | 0.04 | — | 0.04 |
| Alloocimene | 0.07 | — | 0.03 |
| Benzyl Acetate | 0.06 | 0.29 | 0.27 |
| Octanoic Acid | — | 0.01 | — |
| Nerol Oxide | 0.06 | — | 0.07 |
| Methyl Acetophenone | — | 0.23 | — |
| Phenyl Propionaldehyde | — | — | 0.03 |
| Cis-3-Hexenyl Butyrate | — | 0.1 | — |
| Methyl Salicylate | — | 7.04 | 1.79 |
| Anethole | 0.01 | — | 0.03 |
| Citronellal | — | 0.01 | — |
| Citronellol | — | — | 2.5 |
| Phenylacetaldehyde Oxime | — | 0.03 | — |
| Nerol | 2.3 | — | 2.5 |
| Phenethyl Acetate | 10.96 | — | 7.02 |
| Geraniol | — | — | 1.5 |
| Neral | — | 0.13 | 3.07 |
| 3,5-Dimethoxy Toluene | 29.55 | — | 6.58 |
| Geranial | — | — | 1.0 |
| 2-Phenylnitromethane | — | 1.57 | 0.26 |
| Indole | — | 6.82 | 0.2 |
| Theaspirane | 0.01 | — | 0.01 |
| Methyl Anisate | — | — | 0.51 |
| Benzyl Butyrate | — | 0.01 | — |
| Methyl Geranate | 0.17 | — | 0.2 |
| Eugenol | 0.05 | — | 0.01 |
| Citronellyl Acetate | 0.27 | — | 0.71 |
| Neryl Acetate | 0.71 | — | 0.29 |
| Methyl Cinnamate | — | 0.05 | — |
| Alpha Cubebene | 0.21 | — | 0.03 |
| Geranyl Acetate | 5.42 | — | 2.2 |
| Cis-Jasmin | — | 1.04 | 0.1 |
| Amyl Benzoate | — | 0.15 | — |
| Methyl Eugenol | 1.27 | — | 0.56 |
| Cyclotridecanone (T) | — | 1.41 | — |
| Alpha-Copaene | 0.75 | — | 0.08 |
| Beta-Bourbonene | 0.02 | — | 0.02 |
| Beta-Caryophellene | 1.43 | — | — |
| Beta-Elemene | — | — | 0.07 |
| Pentyl Benzoate | — | 0.15 | 0.04 |
| Beta-Cubebene | 0.36 | — | 0.97 |
| Geranyl Acetate | — | — | 0.25 |
| D.H. Beta-Ionol | 0.2 | — | 0.2 |
| Gamma-Cadinene | 0.41 | — | 0.48 |
| Germacrene D | 13.59 | — | 2.06 |
| Gamma-Elemene | 0.91 | — | — |
| Alpha-Farnesene | — | 4.73 | 5.7 |
| Amyl Salicylate | — | 0.15 | — |
| Calamene | 0.01 | — | — |
| Delta-Cadinene | — | — | 0.25 |
| Nerolidol | — | 2.04 | 0.14 |
| Cis-3-Hexenyl Benzoate | — | 1 | — |
| Beta-Ionone | — | — | 0.04 |
| Delta-Cadinol | 0.02 | — | — |
| Heptadecene | 0.06 | — | 0.01 |
| Myristic Acid | — | 0.02 | — |
| 1-Nonadecene | 0.18 | — | 0.04 |
| Nonadecane | 0.01 | 0.32 | 0.01 |
| Methyl Palmitate | — | 0.14 | — |
| Phenethyl Benzoate | — | 0.01 | — |
| TOTAL PERCENTAGE IDENTIFIED | 88.48 | 89.78 | 94.49 |

T = Tentative Identification

The following perfume formulation was then prepared resulting from the analysis of the combined Jasminum nitidum-peach rose fragrant delight headspace analysis:

| Ingredients | Parts by Weight |
|---|---|
| 3-Methyl butyronitrile | 1.1 |
| Isoamyl acetate | 19.54 |
| 3-Methyl pentanol acetate | 1.81 |
| Cis-3-hexenyl acetate | 1.19 |
| n-Hexyl Acetate | 1.4 |
| Methyl benzoate | 2.3 |
| Beta-phenylethyl alcohol | 1.6 |
| Beta-phenethyl acetate | 7.02 |
| Geraniol | 1.5 |
| Neral | 3.07 |
| 3,5-Dimethoxy toluene | 6.58 |
| Geranial | 1.0 |
| Geranyl acetate | 2.2 |
| Germacrene D | 2.06 |
| Alpha-farnesene | 5.7. |

The resulting fragrance has an intense natural rose and jasmine aroma.

The contents of the traps in each of the experimental runs were analyzed by GC-MS analysis using a 50M×0.032 OV-2 fused silica column having the conditions: 50°–220° C. temperature range at 3° C. per minute.

EXAMPLE II

A procedure was carried out using the apparatus of FIGS. 1A and 1B except that the two flowers used are: yellow osmanthus olive and peach rose fragrant delight.

FIG. 15 is the GC-mass spectrum for the analysis of the headspace over the two flowers contained in the apparatus of FIG. 1. The contents of the trap were analyzed by GC-MS analysis using a 50M×0.32 mm OV-2 fused silica column having the conditions: 50°–220° C. at 3° C. per minute. Table II below sets forth the results of the analysis of the headspace over the two flowers compared with the headspace over the individual flowers separately:

TABLE II

ANALYSIS OF HEADSPACE OVER PEACH COLORED ROSE FRAGRANT DELIGHT AND YELLOW OSMANTHUS SWEET OLIVE

| Compound In BiFlower | Rose + Osmanthus "Biflower" (%) | Rose (%) | Osmanthus (%) |
|---|---|---|---|
| 2-Hexenal | — | — | 0.20 |
| Cis-3-hexenol | 0.02 | — | 0.14 |
| Hexanol, N | Trace | — | 0.03 |
| Isoamyl Acetate | 0.08 | 1.05 | — |
| Cyclohexanone | — | 8.82 | 0.10 |
| Cyclohexen, 1-Acetyl | 0.06 | 0.18 | 0.12 |
| Heptanal, N | 0.08 | — | 0.12 |
| 2-Pentanone, 1-Methoxy-3-Methylene | 0.01 | — | 0.06 |
| Anisol | 0.01 | Trace | — |
| 2-Buten-1-ol, 3-methyl: Acetate | 0.04 | 0.37 | — |
| Methyl Anisol | 0.01 | 0.05 | — |
| Nonane | — | — | 0.05 |
| Benzaldehyde | 0.08 | 2.07 | 0.26 |
| 6-Methyl-5-Heptane-2-One | 1.10 | 1.21 | 0.84 |
| Phenol | 0.15 | 0.15 | — |
| Benzene Methyl Ether | Trace | 0.10 | — |
| 6-Methyl, 5-Hepten-2-ol | 0.01 | 0.10 | — |
| Myrcene | 0.35 | 1.24 | 0.32 |
| Cis-3-Hexenyl Acetate | 2.62 | 1.16 | 0.45 |
| Hexyl Acetate | 0.59 | 0.68 | — |
| Benzyl Alcohol | Trace | 0.05 | Trace |
| 2-Methyl Heptanol | 0.05 | — | — |

TABLE II-continued

ANALYSIS OF HEADSPACE OVER PEACH COLORED ROSE FRAGRANT DELIGHT AND YELLOW OSMANTHUS SWEET OLIVE

| Compound In BiFlower | Rose + Osmanthus "Biflower" (%) | Rose (%) | Osmanthus (%) |
|---|---|---|---|
| Para Methyl Styrene | Trace | — | Trace |
| Limonene | 0.01 | 0.44 | 0.01 |
| 2,6-Octadiene,2,6-Dimethyl | 0.25 | 0.19 | 0.30 |
| Trans Ocimene | 1.37 | 0.32 | 0.42 |
| Linalool Oxide (2) | 0.13 | — | 1.91 |
| Trans Decalin | — | — | 0.04 |
| P-Cymene | 0.02 | — | 0.04 |
| Linalool | 3.83 | — | 50.64 |
| Phenylethyl Alcohol | 3.83 | 2.00 | — |
| Rose Oxide (2) | 0.02 | 0.03 | — |
| Homo Ocimene | 1.69 | — | 1.05 |
| Epoxy Linalool | — | — | 0.32 |
| Terpinolene | 0.04 | 0.03 | — |
| Nerol Oxide | 0.06 | 0.06 | — |
| Benzyl Acetate | — | 0.29 | — |
| Cis-3-Hexenyl Butyrate | 0.11 | — | 0.66 |
| Decanal, N | — | — | 0.42 |
| Methyl Salicylate | 0.11 | — | — |
| Estragol | Trace | Trace | — |
| Citronellol | 3.80 | — | — |
| Nerol | 5.70 | 2.30 | 0.39 |
| Neral | — | — | 0.11 |
| Phenyl Ethyl Acetate | 4.36 | 11.00 | — |
| Geraniol | 31.38 | — | 17.20 |
| Geranial | — | — | 0.74 |
| 3,5-Dimethoxy Toluene | 13.58 | 29.50 | — |
| Tridecane, N | — | — | 0.03 |
| Theaspirane | 0.02 | Trace | — |
| Ethanol-2-(P-Methoxy Phenol) | — | — | Trace |
| Methyl Geranate | 0.03 | 0.17 | — |
| Eugenol | — | 0.05 | — |
| Citronellyl Acetate | 0.56 | 0.27 | — |
| Neryl Acetate | 0.30 | 0.71 | — |
| Alpha-Cubebene | 0.02 | 0.21 | — |
| Geranyl Acetate | 2.16 | 5.42 | — |
| Eugenyl Methyl Ether | 0.42 | 1.27 | — |
| Alpha-Copaene | 0.16 | 0.75 | — |
| Beta-Bourbonene | 0.21 | 0.02 | — |
| Beta-Caryophyllene | — | 1.43 | — |
| Beta-Elemene | 0.31 | — | — |
| Dihydro Alpha-Ionone | 0.07 | — | 0.12 |
| Alpha-Ionone | 0.04 | — | 0.22 |
| Unknown Sesquirterpene | 1.31 | — | — |
| Dihydro-Beta-Ionone | 1.32 | — | 5.74 |
| Gamma-Decalactone | 0.10 | — | 0.59 |
| Dihydro-Beta-Ionol | 1.62 | 0.20 | 0.59 |
| Dedecanol, N | — | — | 0.22 |
| Beta-Ionone Epoxide | — | — | Trace |
| Beta-Ionone | 0.12 | — | 1.18 |
| Germacrene-D | 4.37 | 13.60 | — |
| Farnesene | — | — | 0.03 |
| Calamenene | 0.08 | Trace | — |
| Delta-Cadinene | 0.52 | — | — |
| Alpha-Calacorene | 0.01 | — | — |
| Hxadecane, N | 0.04 | Trace | — |
| Tert Muurolol | 0.03 | — | — |
| Alpha-Cadinol | 0.03 | 0.02 | — |
| Heptadecene | 0.23 | 0.06 | — |
| Heptadecane, N | 0.17 | 0.03 | — |
| Octadecene | 0.03 | Trace | — |
| Nonadecene | 1.35 | Trace | — |
| Nonadecane | 0.14 | Trace | — |
|  | 91.42 | 87.60 | 85.62 |

As a result of the foregoing analysis as set forth in Table II, the following fragrance formulation was prepared using the major components of the "biflower" headspace:

| Ingredients | Parts by Weight |
|---|---|
| 6-Methyl-5-heptane-2-one | 1.10 |
| Cis-3-hexenyl acetate | 2.62 |
| Trans ocimene | 1.37 |
| Linalool | 3.83 |
| Beta-phenylethyl alcohol | 3.83 |
| Citronellol | 3.80 |
| Nerol | 5.70 |
| Beta-phenylethyl acetate | 4.36 |
| Geraniol | 31.38 |
| 3,5-Dimethoxy toluene | 13.58 |
| Geranyl acetate | 2.16 |
| Dihydro-beta-ionone | 1.32 |
| Dihydro-beta-ionol | 1.62 |
| Germacrene-D | 4.37 |
| 1-Nonadecene | 1.35. |

The resulting fragrance has an intense and substantitive natural lilac and rose aroma. The fragrance can be described as a "floral fragrance with lilac and rose topnotes and undertones".

EXAMPLE III

Headspace Analysis and Perfume Formulation Resulting Therefrom Using Ginger Lily Flower and *Jasminum odoratissimum* Flower A procedure was carried out identical to that of Example I in the apparatus of FIGS. 1A and 1B with the exception that the two flowers used in the apparatus are ginger lily flower and *Jasminum odoratissimum* flower.

The GC-mass spectral analysis is set forth in FIG. 16.

A perfume formulation was prepared containing the major components of the analysis, to wit:

Cis-3-hexenyl acetate;
Trans-2-hexenyl acetate;
Linalool;
Trans-beta-ocimene;
Benzyl acetate;
Beta-phenylethyl acetate;
Methyl salicylate; and
Germacrene D.

The resulting formulation can be described as "floral fragrance with ginger and jasmine topnotes and ginger and jasmine undertones".

EXAMPLE IV

Analysis of Biflower Headspace Using Purple *Heliotropium iowa* and *Jasminum odoratissimum* Flower A procedure identical to that of Example I was carried out with the exception that the two flowers used in this example are purple *Heliotropium iowa* and *Jasminum odoratissimum* flower. The GC-mass spectral analysis for the headspace from purple *Heliotropium iowa* and *Jasminum odoratissimum* flower is set forth in FIG. 17.

A fragrance formulation was prepared using the major components resulting from the analysis as set forth in FIG. 17 and the fragrance formulation contains:

Cis-3-hexenol;
Trans-2-hexenol;
Benzaldeyde;
Cis-3-hexenyl acetate;
Trans-2-hexenyl acetate;
Benzyl alcohol;
Methyl benzoate;

Linalool;
Benzyl cyanide;
Benzyl acetate;
Methyl salicylate;
Anisaldehyde;
Beta-phenylethyl acetate;
Indole; and
Alpha-farnesene.

The resulting product can be described as "a floral fragrance having sweet, green, lilac and Hawthorne topnotes and fruity and jasmine undertones".

EXAMPLE V

Analysis and Fragrance Preparation of Biflower Fragrance Using the Dwarf Navel Orange Flower and the *Jasmin nitidum* Flower An analysis and procedure was carried out identical to that of Example I with the exception that the two flowers contained in the totally enclosed 3-space of the apparatus are: the dwarf navel orange flower and the jasmin nitidum flower.

The analysis of the headspace is set forth in the GC-mass spectrum of FIG. 18.

The major components of the GC-mass spectrum of FIG. 18 are then obtained and admixed and these components are as follows:

Myrcene;
2-Cyanobutane;
Benzyl alcohol;
Limonene;
Trans-beta-ocimene;
Methyl benzoate;
Linalool;
Beta-phenylethyl alcohol;
Methyl salicylate;
Methyl anthranilate;
Cis-jasmone;
Beta-caryophyllene;
Beta-selinene; and
Alpha-farnescene.

The resulting fragrance can be described as having a floral aroma with orange flower and green topnotes and green and jasmine undertones.

EXAMPLE VI

Analysis and Fragrance Preparation Using as the "Biflower" the Red Nose All that Jazz and the White Ginger Lily Flower A procedure was carried out identical to that of Example I with the exception that the two flowers contained in the headspace of the totally enclosed 3-space are the (i) red rose all that jazz and (ii) the white ginger lily flower.

The analysis of the resulting headspace is set forth in the GC-mass spectrum of FIG. 19.

As a result of the foregoing analysis the major components of this analysis were obtained and formulated into a fragrance. These major components are as follows;

3-Methyl butyronitrile;
2-Pentanal;
Pentanal oxime;
2,5-Dihydro-3-methyl furan;
Myrcene;
Limonene;
Cis-Ocimene;
Trans-ocimene;
Methyl benzoate;
4,8-Dimethyl-1,3,7-nonatriene;
3,5-Dimethoxy toluene;
Cis-jasmone;
Germacrene-D;
Alpha-farnesene; and
1-Nonadecene.

The resulting fragrance can be described as "floral having rose, ginger and lily topnotes and rose, ginger and lily undertones".

EXAMPLE VII

Preparation of a Soap Composition

100 Grams of soap chips are admixed with 1 gram of one of the perfume substances of Table III below until a substantially homogeneous composition is obtained. The perfumed soap manifests an excellent aroma as set forth in Table III below:

TABLE III

| Perfume Ingredients | Aroma |
| --- | --- |
| Perfume composition of Example I. | An intense natural rose and jasmine aroma. |
| Perfume composition of Example II. | A floral fragrance having rose with lilac and rose topnotes and undertones. |

EXAMPLE VIII

Preparation of a Cologne and Handkerchief Perfume

One of the perfume substances are set forth in Table III of Example VII is incorporated into a cologne at concentrations of 1.5%, 2.0%, 2.5%, 3.0%, 3.5% and 4.0% in 80%, 85%, 90% and 95% aqueous ethanol and into handkerchief perfumes at concentrations of 15%, 20%, 25% and 30% (in 85%, 90% and 95% aqueous ethanol). Distinct and definite fragrances as set forth in Table III of Example VII are imparted to the cologne and to the handkerchief perfume at each of the levels indicated.

EXAMPLE IX

Preparation of a Cosmetic Powder Composition

A cosmetic powder is prepared by mixing in a ball mill, 100 grams of talcum powder with 0.15 grams of one of the substances of Table III of Example VII. The resulting powders have excellent aromas as set forth in Table III of Example VII.

EXAMPLE X

Utilizing the procedure of Example I of Column 15 U.S. Pat. No. 3,632,396 the specification for which is incorporated by reference herein, a non-woven cloth substrate useful as a drier-added fabric-softening article of manufacture is prepared wherein the substrate, the substrate coating and the outer coating and the perfuming material are as follows:

1. a water "dissolvable" paper ("Dissolvo paper");
2. Adogen 448 (m.p. about 140° F.) as the substrate coating; and
3. an outer coating having the following formulation (melting point about 150° F.):

57 percent—C$_{20-22}$HAPS (3-(N-alkyl-N,N-dimethylammonio)-2-hydroxypropane-1-sulfonate, wherein the alkyl is a mixture of alkyls having from 20 to 22 carbon atoms)
27 percent—isopropyl alcohol
20 percent—antistatic agent
1 percent—of one of the perfume substances of Table III of Example VII.

Fabric-softening compositions prepared as set forth above having an aroma characteristic as set forth in Table III of Example VII essentially consists of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and a summed outer coating weight ratio of about 1:1 by weight of the substrate. Aromas are imparted as set forth in Table III of Example VII in a pleasant manner to the headspace in the dryer on operation thereof using the said dryer added fabric softening non-woven fabric.

EXAMPLE XI

Preparation of a Soap Composition

100 Grams of soap chips are prepared according to Example V of U.S. Pat. No. 4,058,490 issued on Nov. 15, 1977 the specification for which is incorporated herein by reference, as follows:

"The sodium salt of an equal mixture of C$_{10}$-C$_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-C$_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water 0.2 lb. titanium hydroxide."

The resulting blend is then mixed with one of the perfume substances of Table III of Example VII until a substantially homogeneous composition is obtained. The perfumed soap composition manifests an aroma as set for in Table III of Example VII.

EXAMPLE XII

Granular Detergent Composition

A granular detergent composition is prepared according to United Kingdom Patent No. 1,501,498 the specification for which is incorporated by reference herein having the following formula. It is prepared by spray-drying the following mixture:

| Ingredient | Parts by Weight |
|---|---|
| Sodium salt of ethoxylated fatty alcohol sulfate having an average of about 2.25 moles of ethylene oxide per mole of fatty alcohol | 14.1 |
| Sodium tallow alkyl sulfate | 2.4 |
| Sodium silicate solids ratio SiO$_2$/Na$_2$O = 2.0 | 6.0 |
| Sodium tripolyphosphate | 24.0 |
| Na$_{12}$(AlO$_2$SiO$_2$)27H$_2$O | 18.0 |
| Moisture | 10.0 |
| Sodium sulfate | 25.0 |
| Perfume substance of Table III of Example VII | 4.0 |

Laundry solutions containing the above detergent compositions are used to launder fabrics. Each of the laundry compositions both prior to and on laundering give rise to a pleasant aroma as set forth in Table III of Example VII.

EXAMPLE XIII

Perfumed Liquid Detergent

Concentrated liquid detergents are prepared with aromas as set forth in Table III of Example VII containing 0.10%, 0.15% and 0.20% of each of the substances of Table III of Example VII in the liquid detergent. The liquid detergent is a builder free liquid detergent consisting of (a) 50% of a nonionic surfactant having a HBL (hydrophilic-lipophile balance) of 8.0 and a critical micelle concentration of 0.007 weight percent at 25° C.; (b) an anionic surfactant which is a triethanolamine prepared according to United Kingdom Patent No. 1,491,603 the specification for which is incorporated by reference herein.

The detergents all possess aromas as set forth in Table III of Example VII, supra.

EXAMPLE XIV

Preparation of a Detergent Composition

A total of 100 grams of detergent powder (a low phosphate content detergent composition which contains 12% by weight phosphate builder, 8 percent hardness mineral ion insensitive detergent, 0.9 percent by weight maleic anhydride-vinyl compound co-polymer and 2 percent alkylene oxide condensation product prepared according to Example IV at column IX, U.S. Pat. No. 4,000,080 issued on Dec. 28, 1976, the specification for which is incorporated by reference herein) is intimately admixed with 0.15 grams of one of the perfume materials of Table III of Example VII, supra, until a substantially homogeneous composition is obtained. The composition has an aroma as set forth in Table III of Example VII, supra.

EXAMPLE XV

Each of the fragranced material of Table III of Example VII, supra, are added to a 50:50 weight:weight mixture of low density polyethylene:polyepsilon caprolactone PCL-700 forming pellets with scents as set forth in Table III of Example VII, supra.

75 Pounds of a mixture of PCL-700 polyepsilon caprolactone (manufactured by the Union Carbide Corporation of New York, N.Y. having a melting point of about 180°-190° F.): low density polyethylene are heated to about 250° C. in a container of the kind illustrated in FIGS. 24 and 25. 25 Pounds of each of the fragrance materials as set forth in Table III of Example VII is then quickly added to the liquified polymer mixture, the lid 228 is put in place and the agitating means 273 are actuated. The temperature is then raised to about 260° F. and the mixing is continued for 5–15 minutes. The valve "V" is then opened to allow flow of the molten polymer enriched with perfume ingredient to exit through the orifices 234. The liquid falling through the orifices 234 solidified almost instantaneously upon impact with the moving cooled conveyor 238. Polymer beads or pellets 244 having pronounced scents as described in Table III of Example VII, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table III of Example VII, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table III of Example VII, supra.

EXAMPLE XVI

Each of the LIVING FLOWER ® perfume compositions of Table III of Example VII are individually admixed with CLARYCET TM (trademark of International Flavors & Fragrances Inc. for the ester having the structure:

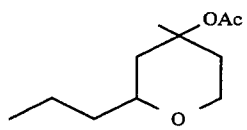

in the ratio of 10 parts by weight of ester to one part by weight of LIVING FLOWER ® perfume composition. At the rates of:

100 ppm;
150 ppm; and
200 ppm the resulting composition is added to EXXON ® middle distillate fuel heating oil in accordance with the procedure of European Published Application 532556 published on Mar. 24, 1990 (corresponding to PCT Application 91/18961-A).

On use, in each case, the unpleasant "burnt fuel oil" nuances are completed masked and "faint pleasant aromas" described in Table III of Example VII are imparted to the environments surrounding the burning heating oil.

What is claimed is:

1. A process for qualitatively and quantitatively substantially continuously analyzing the emitted aroma and rates of emission of the aroma components thereof from a plurality of n members of two or more different species and/or varieties of living flowers wherein n is an integer greater than or equal to 2, each of which living flower is attached through a stem to a living plant or a living tree, said plurality of n members being located within a single totally enclosed 3-space having an outer side and an inner side, said inner side entirely surrounding all of said n living flowers comprising the steps of:
   (a) providing a hollow enclosure having
      (i) an outer wall containing at least n+1 outer wall orifices spaced at a distance of at least $d_1$ from one another in order to provide for the unobstructed individual maintenance of each of the living flowers, each orifice having an orifice wall surrounding said orifice;
      (ii) having an inner void having a volume $V_0$ sufficient to provide for the separate individual unobstructed maintenance of each of the living flowers; and
      (iii) having an inner volume $V_0$ such that the volume relationship between the volume of the inner void expressed as "$V_0$" and the volume of the 3-space surrounding each living flower, "$V_i$", the individual flower surrounding 3-space is:

$$V_0 > \sum_{i=2}^{n} V_i$$

wherein $$V_i = \frac{4}{3} \pi R_i^3;$$

$$V_0 > \sum_{i=2}^{n} \frac{4}{3} \pi R_i^3;$$

and $$V_0 = H + \sum_{i=2}^{n} \frac{4}{3} \pi R_i^3$$

the mathematically constructed sphere having a volume $V_i$ having an individual mathematically constructed outer surface and $$\sum_{i=2}^{n} V_i$$

having a mathematically constructed outer surface wherein $R_i$ represents the length of the longest petal of the $i^{th}$ living flower and H is the headspace between the outer surface of $$\sum_{i=2}^{n} V_i$$

and said inner wall of said single totally enclosed 3-space;
   (b) causing the insertion of each of the n members of the plurality of living flowers through a separate outer wall orifice whereby the stem of each living flower is held in place by means of the gripping action of the orifice wall of each of said orifices and whereby each living flower is held in place within said hollow enclosure with the mathematically constructed surface $S_i$ of each living flower being at a finite distance $d_2$ from its assigned orifice; in contact with at least one of its neighboring flowers and/or at a finite distance $d_3$ from each of the mathematically constructed surfaces $S_i$ of each of its neighboring living flowers; and at a finite distance $d_4$ from any inner wall of said hollow enclosure,
   (c) trapping the components of said emitted aroma, in trapping tube means containing a trapping material, said trapping tube means being engaged with a juxtaposed to at least one of said orifices at a location outside said hollow enclosure, said trapping tube means having two ends; (i) an orifice end sealably juxtaposed with and engaging said orifice wall and (ii) an outer end at a location outside said hollow enclosure;

(d) exerting a negative pressure on said single totally enclosed 3-space using a vacuum pumping means, said vacuum pumping means being juxtaposed with and engaging said outer end of said trapping tube means, whereby said aroma components are transmitted from said single totally enclosed 3-space into said trapping tube means and onto said trapping material thereby forming an aroma component-bearing trapping material;

(e) removing the aroma component-bearing trapping material from said trapping tube means;

(f) extracting the aroma components from the aroma component-bearing trapping material thereby forming an extracted aroma component composition; and (g) carrying out qualitative and quantitative analysis on the extracted aroma component composition.

2. The process of claim 1 wherein steps (e), (f) and (g) are carried out over a period of time, repetitively at the end of specific time intervals.

3. A process for preparing a plurality of separate perfume compositions comprising the steps of:
(i) carrying the process of claim 2;
(ii) separately providing from independent sources at least the major aroma components found by the analyses of step (g) of claim 2; and
(iii) separately admixing each of the groups of components provided by (ii).

4. The process for preparing a perfume composition comprising the steps of:
(i) carrying out the process of claim 1;
(ii) providing from at least one independent source at least the major aroma components found by the analysis of step (g) of claim 1; and
(iii) admixing the components provided by (ii).

5. The perfume composition produced according to the process of claim 4.

6. A perfumed article comprising a perfumed article base and an aroma augmenting, enhancing or imparting quantity of the composition defined according to claim 5.

7. A cologne consisting essentially of water, ethanol and the composition defined according to claim 5.

8. The process of claim 1 wherein said single totally enclosed 3-space is in the shape of a sphere.

9. A process for preparing a perfume composition comprising the steps of:
(i) carrying out the process of claim 1 wherein said single totally enclosed 3-space is in the shape of a sphere;
(ii) providing from at least one independent source at least the major aroma components found by the analysis of step (g) of claim 1; and
(iii) admixing the components provided by (ii).

10. The process of claim 1 wherein said single totally enclosed 3-space is in the shape of a right circular cone.

11. The process for preparing a perfume composition comprising the steps of:
(i) carrying out the process of claim 1 wherein said single totally enclosed 3-space is in the shape of a right circular cone;
(ii) providing from at least one independent source at least the major aroma components found by the analysis of step (g) of claim 1; and
(iii) admixing the components provided by (ii).

12. The process of claim 1 wherein said single totally enclosed 3-space is in the shape of an ellipsoid.

13. The process of claim 12 wherein the volume relationship:

$$V_0 > \sum_{i=2}^{n} V_i$$

is such that:

$$V_0 = 8 \int_0^{\sqrt{\frac{k}{a}}} \int_0^{\sqrt{\frac{k^2}{b} - \frac{ax^2}{b}}} \int_0^{\sqrt{\frac{k^2}{c} - \frac{ax^2}{c} - \frac{by^2}{c}}} dz\,dy\,dx$$

wherein the equation for the ellipsoid is:

$$ax^2 + by^2 + cz^2 = K^2$$

wherein a, b, c and k are the same or different numerical constants; wherein x is a dimensional variable measuring horizontal distance from the geometric center of said ellipsoid to said inner side of said hollow enclosure; wherein y is a dimensional variable measuring the vertical distance from the geometric center of said ellipsoid to said inner side of said hollow enclosure; and wherein z is a dimensional variable measuring the depth distance from the geometric center of said ellipsoid to said inner side of said hollow enclosure.

14. The perfume composition produced according to the process of claim 13.

15. A process for preparing the perfume composition comprising the steps of:
(i) carrying out the process of claim 1 wherein said single totally enclosed 3-space is in the shape of an ellipsoid;
(ii) providing from at least one independent source at least the major aroma components found by the analysis of step (g) of claim 1; and
(iii) admixing the components provided by (ii).

16. The process of claim 1 wherein said single totally enclosed 3-space is in the shape-of a right circular cylinder.

17. A process for preparing a perfume composition comprising the steps of:
(i) carrying out the process of claim 1 wherein said single totally enclosed 3-space is in the shape of a right circular cylinder;
(ii) providing from at least one independent source at least the major aroma components found by the analysis of step (g) of claim 1; and
(iii) admixing the components provided by (ii).

18. The process of claim 1 wherein said single totally enclosed 3-space is in the shape of a frustum of a right circular cone.

19. A process for preparing a perfume composition comprising the steps of:
(i) carrying out the process of claim 1 wherein said single totally enclosed 3-space is in the shape of a frustum of a right circular cone;
(ii) providing from at least one independent source at least the major aroma components found by the analysis of step (g) of claim 1; and
(iii) admixing the components provided by (ii).

20. The process of claim 1 wherein said single totally enclosed 3-space is in the shape of a rectangular parallelepiped.

21. A process for preparing a perfume composition comprising the steps of:
   (i) carrying out the process of claim 1 wherein said single totally enclosed 3-space is in the shape of a rectangular parallelepiped;
   (ii) providing from at least one independent source at least the major aroma components found by the analysis of step (g) of claim 1; and
   (iii) admixing the components provided by (ii).

22. The process of claim 1 wherein said single totally enclosed 3-space is in the shape of a tetrahedron.

23. A process for preparing a perfume composition comprising the steps of:
   (i) carrying out the process of claim 1 wherein said single totally enclosed 3-space is in the shape of a tetrahedron;
   (ii) providing from at least one independent source at least the major aroma components found by the analysis of step (g) of claim 1; and
   (iii) admixing the components provided by (ii).

24. The process of claim 1 wherein radiation from one or more radiation sources connected to an electric power supply is emitted in a direction from said one or more radiation sources and is directed into said totally enclosed 3-space.

25. The process of claim 24 wherein the radiation source is an infrared radiation source.

26. The process of claim 24 wherein the radiation source is an ultraviolet radiation source.

27. The process of claim 24 wherein the radiation sources are two in number (i) an infrared radiation source and (ii) an ultraviolet source.

28. The perfume composition produced according to the process of claim 24.

29. Apparatus for qualitatively and quantitatively substantially continuously analyzing the emitted aroma and rates of emission of the aroma components thereof from a plurality of n members of two or more different species and/or varieties of living flowers wherein n is an integer greater than or equal to 2, each of which living flower is attached through a stem to a living plant or a living tree, said plurality of n members being located within a single totally enclosed 3-space having an outer side and an inner side, said inner side entirely surrounding all of said n living flowers comprising:
   (a) two or more adjacently located species and/or varieties of living flowers each of which is attached through a stem to a living plant imbedded in a nutrient medium;
   (b) a hollow enclosure having:
      (i) an outer wall containing at least $n+1$ outer wall orifices spaced at a distance of at least $d_1$ from one another in order to provide for the unobstructed individual maintenance of each of the said living flowers, each orifice having an orifice wall surrounding said orifice;
      (ii) having an inner void having a volume $V_0$ sufficient to provide for the separate individual unobstructed maintenance of each of said living flowers; and
      (iii) having an inner volume $V_0$ such that the volume relationship between the volume of the inner void expressed as "$V_0$" and the volume of the 3-space surrounding each living flower, $V_i$, the individual flower surrounding 3-space is:

$$V_0 > \sum_{i=2}^{n} V_i$$

wherein $$V_i = \frac{4}{3} \pi R_i^3;$$

$$V_0 > \sum_{i=2}^{n} \frac{4}{3} \pi R_i^3;$$

and $$V_0 = H + \sum_{i=2}^{n} \frac{4}{3} \pi R_i^3;$$

$V_i$ having an individual mathematically constructed outer surface and $$\sum_{i=2}^{n} V_i$$

having a mathematically constructed outer surface wherein $R_i$ represents the length of the longest petal of the $i^{th}$ living flower and H is the headspace between the mathematically constructed outer surface of $$\sum_{i=2}^{n} V_i$$

and said inner wall of said single totally enclosed 3-space, each of the end members of the plurality of living flowers being inserted through a separate outer wall orifice whereby the stem of each living flower is held in place by means of the gripping action of the orifice wall of each of the said orifices and whereby each living flower is held in place within the said hollow enclosure with the mathematically constructed surface, $S_i$ of each living flower being at a finite distance $d_2$ from its assigned orifice; in contact with at least one of its neighboring living flowers and/or at a finite distance $d_3$ from each of the mathematically constructed surfaces $S_i$ of each of its neighboring living flowers; and at a finite distance $d_4$ from any inner wall of said hollow enclosure, (c) engaged with and juxtaposed to at least one of said orifices a location outside said hollow enclosure, trapping tube means containing a trapping material for trapping the components of said emitted aroma, said trapping tube means having two ends; (i) an orifice end sealably juxtaposed with and engaging said orifice wall; and (ii) an outer end at a location outside said hollow enclosure end;

(d) juxtaposed with and engaging said outer end of said trapping tube means, a vacuum pumping means exerting a negative pressure on said single totally enclosed 3-space whereby said aroma components are transmitted from said single totally enclosed 3-space into said trapping tube means and onto said trapping material thereby forming an aroma component-bearing trapping material;

(e) means for removing the aroma component-bearing trapping material from said trapping tube means;

(f) extraction means for extracting the aroma components from the aroma component-bearing trapping material thereby forming an extracted aroma component composition; and (g) analysis means for carrying out qualitative and quantitative analyses on the extracted aroma component composition.

30. The apparatus of claim 29 wherein said single totally enclosed 3-space is in the shape of a sphere.

31. The apparatus of claim 29 wherein said single totally enclosed 3-space is in the shape of a right circular cone.

32. The apparatus of claim 29 wherein said single totally enclosed 3-space is in the shape of an ellipsoid.

33. The apparatus of claim 32 wherein the volume relationship:

$$V_0 > \sum_{i=2}^{n} V_i$$

is such that:

$$V_0 = 8 \int_0^{\frac{k}{\sqrt{a}}} \int_0^{\sqrt{\frac{k^2}{b} - \frac{ax^2}{b}}} \int_0^{\sqrt{\frac{k^2}{c} - \frac{ax^2}{c} - \frac{by^2}{c}}} dz\,dy\,dx$$

wherein the equation for the ellipsoid is:

$$ax^2 + by^2 + cz^2 = K^2$$

wherein a, b, c and k are the same or different numeral constants, wherein x is a dimensional variable measuring horizontal distance from the geometric center of said ellipsoid to said inner side of said hollow enclosure, wherein y is a dimensional variable measuring vertical distance from the geometric center of said ellipsoid to said inner side of said hollow enclosure and wherein z is a dimensional variable measuring depth distance from the geometric center of said ellipsoid to said inner side of said hollow enclosure.

34. The apparatus of claim 29 wherein said single totally enclosed 3-space is in the shape of a right circular cylinder.

35. The apparatus of claim 29 wherein said single totally enclosed 3-space is in the shape of a frustum of a right circular cone.

36. The apparatus of claim 29 wherein said single totally enclosed 3-space is in the shape of a rectangular parallelepiped.

37. The process of claim 29 wherein said single totally enclosed 3-space is in the shape of a tetrahedron.

38. The apparatus of claim 29 having in addition, means admixing at least the major components determined using the trapping tube means.

39. The apparatus of claim 29 wherein baffles protrude in a direction from the inner side of said totally enclosed 3-space toward the center of said totally enclosed 3-space.

40. The apparatus of claim 29 having one or more radiation sources requiring an electric power supply said radiation source being external to and in close proximity to said totally enclosed 3-space, radiation from said radiation source being directed into said totally enclosed 3-space.

41. The apparatus of claim 40 wherein the radiation source is an infrared radiation source.

42. The apparatus of claim 40 wherein the radiation source is an ultraviolet radiation source.

43. The apparatus of claim 40 wherein the radiation sources are two in number (i) an infrared radiation source and (ii) an ultraviolet source.

44. The apparatus of claim 29 wherein the walls of said totally enclosed 3-space consist of a transparent elastic semirigid plastic.

45. The apparatus of claim 29 wherein at least two of the two or more adjacently located living flowers are juxtaposed in a contacting manner and $d_3$ is 0.

46. The apparatus of claim 29 wherein at least two of the two or more adjacently located living flowers are juxtaposed in a non-contacting manner.

47. The apparatus of claim 46 wherein the wall of said totally enclosed 3-space is bifurcated.

* * * * *